US012797071B2

(12) United States Patent
Li

(10) Patent No.: US 12,797,071 B2
(45) Date of Patent: Nov. 17, 2026

(54) END-EFFECTOR ASSEMBLY, INITIAL POSITION RETAINER, AND SURGICAL INSTRUMENT

(71) Applicant: REACH SURGICAL, INC., Tianjin (CN)

(72) Inventor: Shuaishuai Li, Tianjin (CN)

(73) Assignee: REACH SURGICAL, INC., Tianjin (CN)

(*) Notice: Subject to any disclaimer, the term of this patent is extended or adjusted under 35 U.S.C. 154(b) by 0 days.

(21) Appl. No.: 19/240,087

(22) Filed: Jun. 17, 2025

(65) Prior Publication Data

US 2025/0312042 A1 Oct. 9, 2025

Related U.S. Application Data

(63) Continuation of application No. PCT/CN2023/139754, filed on Dec. 19, 2023.

(30) Foreign Application Priority Data

Dec. 19, 2022 (CN) ........................ 202211632874.X

(51) Int. Cl.
*A61B 17/00* (2006.01)
*A61B 17/072* (2006.01)
*A61B 90/00* (2016.01)

(52) U.S. Cl.
CPC ........ *A61B 17/07207* (2013.01); *A61B 90/03* (2016.02); *A61B 2017/00367* (2013.01);
(Continued)

(58) Field of Classification Search
CPC .............. A61B 17/07207; A61B 90/03; A61B 2090/034; A61B 2017/00367;
(Continued)

(56) References Cited

U.S. PATENT DOCUMENTS 10,729,509 B2 * 8/2020 Shelton, IV ........... A61B 34/37
2007/0152014 A1 7/2007 Gillum et al.
(Continued)

FOREIGN PATENT DOCUMENTS

CN 105748125 A 7/2016
CN 110477984 A 11/2019
(Continued)

OTHER PUBLICATIONS

International Search Report and Written Opinion received for PCT Patent Application No. PCT/CN2023/139754, mailed on Mar. 15, 2024, 15 pages (6 pages of English Translation and 9 pages of Original Document).

*Primary Examiner* — Jacob A Smith
(74) *Attorney, Agent, or Firm* — ArentFox Schiff LLP; Michael Fainberg

(57) ABSTRACT

The end-effector assembly of the surgical instrument includes: a proximal body portion that defines a longitudinal axis; and a distal execution portion that is adapted to manipulate tissues and is pivotally connected to the proximal body portion through an articulation joint provided with a pivot pin arranged thereon. The proximal body portion includes an articulation transmission member. An articulation drive member is arranged on the articulation joint. The articulation transmission member acts on the articulation drive member to provide an articulation drive force to the articulation joint, so that the distal execution portion is operated to articulated relative to the longitudinal axis of the proximal body portion. When the end-effector assembly is in a ready-to-be-loaded position, the distal execution portion forms an included angle not equal to 0° relative to the longitudinal axis. The distal execution portion of the surgical instrument of the present disclosure can achieve large-angle articulation.

18 Claims, 21 Drawing Sheets

(52) U.S. Cl.
CPC ............... *A61B 2017/00477* (2013.01); *A61B 2017/07257* (2013.01); *A61B 2017/07271* (2013.01); *A61B 2090/034* (2016.02)

(58) Field of Classification Search
CPC ........... A61B 2017/00477; A61B 2017/07257; A61B 2017/07271; A61B 2017/2927; A61B 2017/0046; A61B 2017/00473; A61B 2017/2932
USPC ........................................................ 227/175.1
See application file for complete search history.

(56) References Cited

U.S. PATENT DOCUMENTS

| | | | | |
|---|---|---|---|---|
| 2016/0256152 | A1* | 9/2016 | Kostrzewski | A61B 17/42 |
| 2019/0000466 | A1* | 1/2019 | Shelton, IV | A61B 18/1445 |
| 2020/0315622 | A1 | 10/2020 | Kostrzewski et al. | |

FOREIGN PATENT DOCUMENTS

| | | | |
|---|---|---|---|
| CN | 110799129 | A | 2/2020 |
| CN | 211862882 | U | 11/2020 |
| CN | 115153702 | A | 10/2022 |
| GB | 191418655 | A | 7/1915 |
| JP | 2013-146556 | A | 8/2013 |
| JP | 2020-525231 | A | 8/2020 |
| JP | 2021-508274 | A | 3/2021 |

* cited by examiner

END-EFFECTOR ASSEMBLY, INITIAL POSITION RETAINER, AND SURGICAL INSTRUMENT

The present application is a continuation of International Application No. PCT/CN2023/139754, filed on Dec. 19, 2023, which claims priority to Chinese patent application No. 202211632874.X filed with the China National Intellectual Property Administration on Dec. 19, 2022, and entitled "End-Effector Assembly, Initial Position Retainer, and Surgical Instrument", the entire contents of which are incorporated herein by reference.

TECHNICAL FIELD

The present disclosure relates to the field of surgical instruments, and particularly relates to an end-effector assembly, an initial position retainer, and a surgical instrument for clamping, cutting, and stapling tissues.

BACKGROUND

Laparoscopic surgical stapling instruments are commonly used surgical instruments in laparoscopic surgeries and are suitable for anastomosing and cutting tissues. Such instruments generally include a handle assembly, an elongated body assembly, and an end-effector assembly. During the surgery, a portion of the elongated body assembly and the end-effector assembly are advanced into the patient's body through a pathway created by a trocar device, and the doctor can operate the handle assembly to articulate the end-effector assembly to a certain angle relative to the elongated body assembly to adapt to different tissue cutting and anastomosis positions. In some specific laparoscopic surgical environments or procedures, it is often desirable that the end-effector assembly has a larger articulating angle. For example, surgeries remain the primary treatment for mid-to-low rectal cancer located 4-10 cm from the anal verge, with the main procedure being Low Anterior Resection (LAR). Due to human anatomical characteristics, the pelvic cavity is confined and rich in nerve plexuses and blood vessels. During LAR, the end effector assembly is required to provide a larger articulation angle and a smaller bending radius to facilitate a single-stroke transection of the rectum (refer to FIG. 25), thereby achieving a smaller incision and fewer stapling lines, reducing the probability of stapling leakage, and reducing the occurrence of postoperative complications.

Referring to FIGS. 1-2, an end-effector assembly 50 in prior art includes a proximal body portion 50*a* and a distal execution portion 50*b* that are pivotally connected by means of an articulation joint 50*c*. The distal execution portion 50*b* can be articulated leftward (LA) or rightward (RA) to a certain angle relative to a longitudinal axis C defined by the proximal body portion 50*a*. Due to the structure of this symmetric articulation joint design, such as mechanical interference between components, the maximum articulation angle is typically limited to no more than 50 degrees articulation joint. Furthermore, end effectors in prior art achieving large articulation angles via dual or multi-joint mechanisms employ progressive bending around multiple pivot axes. In addition, although the end-effector assembly in prior art, which achieves large-angle articulating by means of dual or multi-joint mechanisms, has a larger articulating angle due to the use of multiple pivot pins for progressive articulating. While this provides a larger articulation angle, it simultaneously increases the length of the joint section and enlarges the bending radius of the end effector assembly. Consequently, it still cannot adapt to confined surgical environments such as the pelvic cavity.

SUMMARY

It is provided in the present disclosure that an end-effector assembly, comprising a proximal body portion that defines a longitudinal axis; and a distal execution portion adapted to manipulate tissue, wherein the distal execution portion being pivotally connected to the proximal body portion through an articulation joint provided with a pivot pin thereon; the proximal body portion comprises an articulation transmission member, and an articulation drive member is arranged on the articulation joint, wherein the articulation transmission member is pivotably connected to the articulation drive member, and the articulation transmission member is operable to perform reciprocating movement along the direction of the longitudinal axis to actuate the articulation drive member to pivot about the pivot pin and to actuate the distal execution portion to pivot about the pivot pin; and when the end-effector assembly is in a ready-to-be-loaded position, the distal execution portion forms an included angle not equal to 0° relative to the longitudinal axis.

In some embodiments of the present disclosure, when the distal execution portion is operated to extend along the direction of the longitudinal axis, a line connecting an axis center of the articulation drive member and an axis center of the pivot pin forms an angle not equal to 0° with respect to the longitudinal axis.

In some embodiments of the present disclosure, when the distal execution portion is operated to extend along the direction of the longitudinal axis, the articulation drive member is located proximal or distal to the pivot pin.

In some embodiments of the present disclosure, when the end-effector assembly is in the ready-to-be-loaded position, the articulation joint is pivoted so that a line connecting an axis center of the articulation drive member and an axis center of the pivot pin is perpendicular to the longitudinal axis.

In some embodiments of the present disclosure, when the articulation transmission member is operated to move from a start position to an end position, the distal execution portion is actuated to pivot about the pivot pin and to be gradually articulated away from the longitudinal axis.

In some embodiments of the present disclosure, wherein when the articulation transmission member is in the start position, the distal execution portion is operated to extend along the direction of the longitudinal axis.

In some embodiments of the present disclosure, when the end-effector assembly is in the ready-to-be-loaded position, the articulation transmission member is located in an intermediate position that is between the start position and the end position.

In some embodiments of the present disclosure, further comprising a constraint channel adapted to limit an articulation position of a firing member during a firing motion when the distal execution portion is in an articulated state, the constraint channel being arranged in a fitting region between the proximal body portion and the articulation joint, and the firing member being arranged in the constraint channel and movable in a direction in which the constraint channel extends.

In some embodiments of the present disclosure, the constraint channel is formed by a first constraint portion and a second constraint portion arranged on opposite sides of the firing member, respectively.

In some embodiments of the present disclosure, wherein the first constraint portion comprises a first constraint protrusion disposed on the articulation transmission member, the first constraint protrusion has a concave arc surface matching an outer convex arc surface of the firing member when being most articulated, the second constraint portion comprises a second constraint protrusion disposed on the articulation joint, and the second constraint protrusion has a convex arc surface matching an inner concave arc surface of the firing member when being most articulated.

In some embodiments of the present disclosure, wherein the first constraint portion comprises a constraint member disposed on the proximal body portion, the constraint member has a concave arc surface matching an outer convex arc surface of the firing member when being most articulated, the second constraint portion is a convex arc surface provided at the distal end of the articulation transmission member, and the convex arc surface matching an inner convex arc surface of the firing member when being most articulated.

In some embodiments of the present disclosure, a receiving slot is provided in a distal portion of the firing member, and when an articulation angle of the distal execution portion is less than a set value, a partial region of the first constraint portion is received in the receiving slot.

In some embodiments of the present disclosure, the articulation joint comprises a first link and a second link, the pivot pin being disposed on the first link and/or the second link, the first link and the second link are connected through two connection pins located on opposite sides of the pivot pin, and one of the connection pins is adapted for the articulation drive member for cooperating with the articulation transmission member.

In some embodiments of the present disclosure, further comprising an initial position retainer adapted to support the distal execution portion and the proximal body portion so that the distal execution portion is retained in an initial articulated state forming a set angle with respect to the proximal body portion.

In some embodiments of the present disclosure, the initial position retainer comprises a support body having a set angle, and the support body comprises a first holding arm being engaged with the proximal body portion and a second holding arm being engaged with the distal execution portion, and further comprises a supporting beam being connected between the first holding arm and the second holding arm.

In some embodiments of the present disclosure, the initial position retainer is provided with a position-limiting structure for being engaged with the firing member, wherein the position-limiting structure is adapted for being engaged with a working portion of the firing member to limit the position of the firing member.

In some embodiments of the present disclosure, the distal execution portion comprises a staple cartridge assembly and an anvil assembly that are pivotally connected, distal portions of the staple cartridge assembly and the anvil assembly are respectively provided with cooperating positioning structures, the positioning structures being configured to limit lateral positions of the staple cartridge assembly and the anvil assembly along a width direction when the distal effector portion is in a closed position.

In some embodiments of the present disclosure, the positioning structures comprise a positioning protrusion disposed on one of the staple cartridge assembly and the anvil assembly, and a positioning recess disposed on the other of the staple cartridge assembly and the anvil assembly.

In some embodiments of the present disclosure, it is further provided that an end-effector assembly, comprising a proximal body portion defining a longitudinal axis; and a distal execution portion adapted to manipulate tissue, wherein the distal execution portion being pivotally connected to the proximal body portion through an articulation joint provided with a pivot pin thereon; further comprises an articulation transmission member, adapted for actuating an articulation drive member disposed on the articulation joint to provide articulation drive force thereon, so as to further actuate the distal execution portion to articulate to one side relative to the longitudinal axis of the proximal body portion; the distal execution portion is operated to articulate unidirectionally to one side away from the longitudinal axis, and is articulable between an unarticulated position, an intermediate articulated position, and a most articulated position; and the distal execution portion being located at the intermediate articulated position is defined as a ready-to-be-loaded position of the end-effector assembly.

In some embodiments of the present disclosure, it is further provided a surgical instrument, comprising a main body portion and an end-effector assembly that is selectively engaged with the main body portion, and the end-effector assembly is the end-effector assembly according to any embodiments.

In some embodiments of the present disclosure, it is further provided a surgical instrument, comprising an elongated body assembly that defines a longitudinal axis; and a distal execution portion adapted to manipulate tissue, and pivotally connected to the elongated body assembly through an articulation joint provide with a pivot pin arranged thereon; wherein further comprises an articulation transmission member, adapted for actuating an articulation drive member disposed on the articulation joint to provide articulation drive force thereon, so as to further actuate the distal execution portion to articulate to one side relative to the longitudinal axis of the proximal body portion; and when the distal execution portion is operated to extend along the direction of the longitudinal axis, the articulation drive member is located proximal or distal to said pivot pin.

In some embodiments of the present disclosure, it is further provided a surgical instrument, comprising an elongated body assembly that defines a longitudinal axis; and a distal execution portion adapted to manipulate tissue, and pivotally connected to the elongated body assembly through an articulation joint provided with a pivot pin arranged thereon; wherein further comprises an articulation transmission member, adapted for actuating an articulation drive member disposed on the articulation joint to provide articulation drive force thereon, so as to further actuate the distal execution portion to articulate to one side relative to the longitudinal axis of the proximal body portion; and the distal execution portion is operated to articulate unidirectionally to one side away from the longitudinal axis, and is articulatable between an unarticulated position, an intermediate articulated position, and a most articulated position; and the distal execution portion being located at the intermediate articulated position is defined as an initial position of the end-effector assembly.

In some embodiments of the present disclosure, it is further provided an initial position retainer, characterized by comprising a support body having a set angle, so that a distal execution portion of an end-effector assembly of a surgical instrument is retained in an initial articulated state at a set angle with respect to a longitudinal axis.

In some embodiments of the present disclosure, the support body is adapted to be engaged with an end-effector assembly of the surgical instrument, and comprises a first holding arm that engages with a proximal body portion of the end-effector assembly and a second holding arm that engages with a distal execution portion of the end-effector assembly, and an included angle formed by the first holding arm and the second holding arm is an obtuse angle.

In some embodiments of the present disclosure, the support body is adapted to be engaged with an end-effector assembly and an elongated body assembly of the surgical instrument, and comprises a first holding arm that engages with a proximal body portion of the end-effector assembly and a second holding arm that engages with the elongated body assembly, and an included angle formed by the first holding arm and the second holding arm is an obtuse angle.

BRIEF DESCRIPTION OF THE DRAWINGS

The preferred embodiments of the present disclosure will be described in detail below with reference to the drawings, which will help to understand the objects and advantages of the present disclosure, in which.

DETAILED DESCRIPTION

Figure 1:
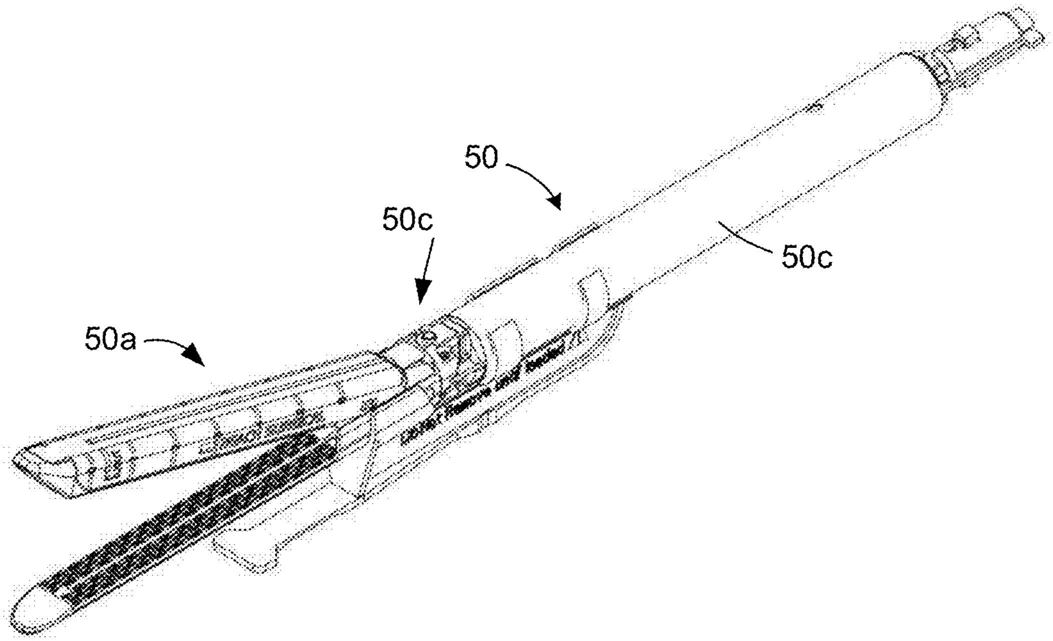
FIG. 1 ( PRIOR ART )
FIG. 1 is a schematic structural diagram of an end-effector assembly of a surgical instrument in the prior art.

The technical solutions of the present disclosure will be clearly and completely described below with reference to the drawings. Obviously, the described embodiments are part of rather than all of the embodiments of the present disclosure. All other embodiments obtained by those of ordinary skill in the art based on the embodiments in the present disclosure without creative efforts shall fall within the scope of protection of the present disclosure.

In the description of the present disclosure, it should be noted that the orientation or positional relationships indicated by the terms "center", "upper", "lower", "left", "right", "vertical", "horizontal", "inner", "outer", and the like are based on the orientation or positional relationships shown in the drawings, and are only for the convenience of describing the present disclosure and simplifying the description, rather than indicating or implying that the device or element referred to must have a specific orientation, or be constructed and operated in a specific orientation, and therefore shall not be construed as a limitation to the present disclosure. In addition, the terms "first", "second", and "third" are used for descriptive purposes only, and shall not be construed as indicating or implying relative importance.

In the description of the present disclosure, it should be noted that, unless explicitly specified and defined otherwise, the terms "mount", "link", and "connect" should be interpreted in a broad sense. For example, they may refer to a fixed connection, a detachable connection, or an integral connection, or may refer to a direct connection, or an indirect connection via an intermediate medium, or may refer to an internal communication of two elements. The specific meanings of the above terms in the present disclosure may be understood by those of ordinary skill in the art in the specific context.

Furthermore, technical features referred to in different embodiments of the present disclosure described below may be combined with each other as long as they do not conflict with each other.

In various embodiments of the present disclosure, "distal end/side" refers to an end of a surgical instrument that is away from an operator when the surgical instrument is operated, and "proximal end/side" refers to an end/side of the surgical instrument that is close to the operator when the surgical instrument is operated.

The following is a specific embodiment of a surgical instrument. In general, the embodiment of the surgical instrument described herein relates to an endoscopic surgical cutting and anastomosis instrument. It should be noted, however, that the surgical instrument may also be a non-endoscopic surgical cutting and stapling instrument, such as an open surgical instrument for open surgeries.

Figure 3:
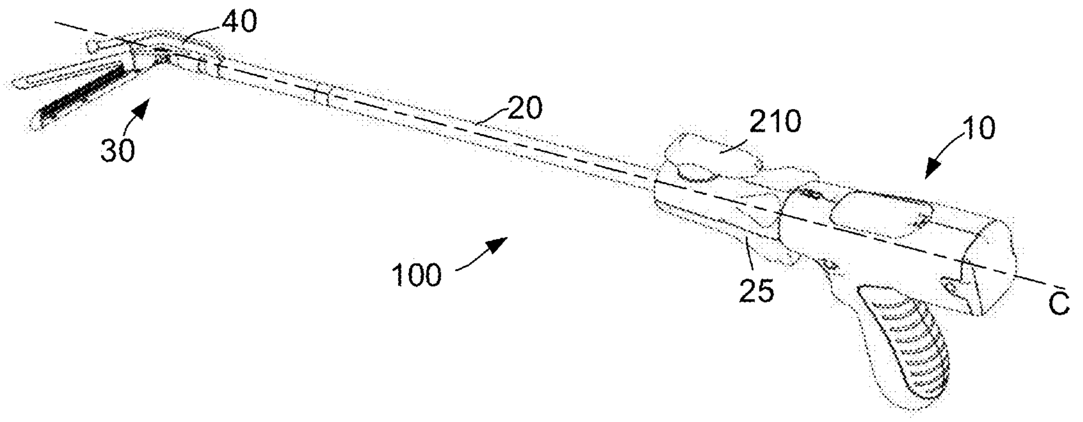
FIG. 3 is a schematic structural diagram of a surgical instrument according to a specific embodiment of the present disclosure.
Figure 4:
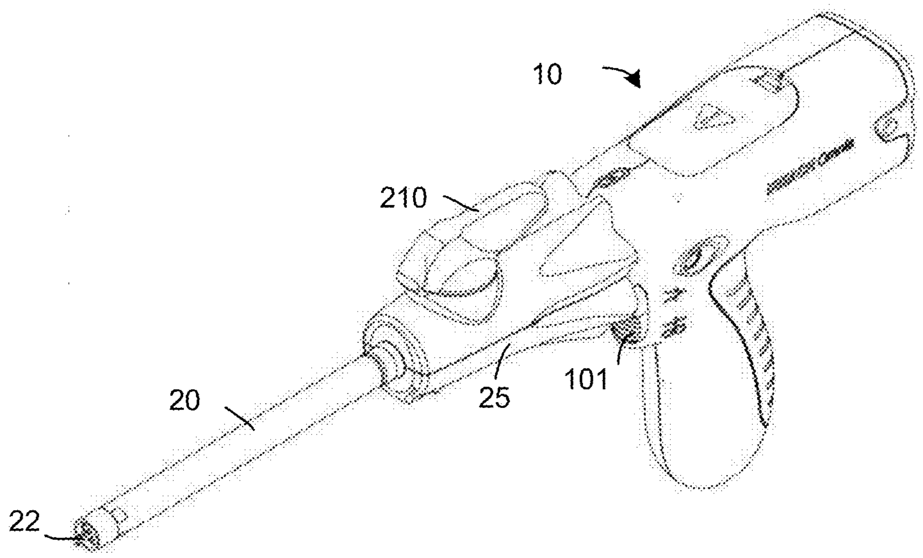
FIG. 4 is a schematic structural diagram of a main body portion of the surgical instrument according to a specific embodiment of the present disclosure.

In particular, FIG. 3 illustrates an embodiment of a surgical instrument 100. The surgical instrument 100 includes a handle assembly 10, an elongated body assembly 20, and an end-effector assembly 30 arranged sequentially from proximal to distal, wherein the elongated body assembly 20 defines a longitudinal axis C and extends distally from the distal end of the handle assembly 10, and the end-effector assembly 30 is coupled with the distal end of the elongated body assembly 20 either detachably or non-detachably. The handle assembly 10 is adapted to allow an operator to manipulate the surgical instrument 100, and the handle assembly 10 may control the end-effector assembly 30 via the elongated body assembly 20 to perform surgical procedures, such as clamping/closing, suturing/stapling, cutting, etc. The handle assembly 10 includes a handle body that can be gripped by the operator in a conventional manner. In a specific embodiment, the surgical instrument 100 controls the closing and firing of the end-effector assembly by means of a trigger. Alternatively, the surgical instrument 100 can also control the closing and firing of the end-effector assembly by means of a push button, a button, or the like disposed on the handle body, so that the end-effector assembly 30 performs cutting and suturing operations. The elongate shaft assembly 20 is tubular and elongate, adapted to transmit driving force provided by the handle assembly to the distal end of the surgical instrument 100.

It should be noted that although the embodiments of the surgical instrument described herein are configured with an end effector assembly for cutting and stapling tissue, in alternative embodiments, other techniques for cutting and stapling tissue can be employed. For example, an end effector utilizing radiofrequency (RF) energy or adhesives to staple tissue could also be used.

The surgical instrument 100 described in the embodiment of the present disclosure further includes a rotation knob 25. The rotation knob 25 is mounted on the distal side of the handle assembly 10, and disposed at the proximal end of the elongated body assembly 20. The rotation knob 25, when being operated to rotate about the longitudinal axis C of the surgical instrument 100, can drive the elongated body assembly 20 and the end-effector assembly 30 to rotate together.

Figure 7:
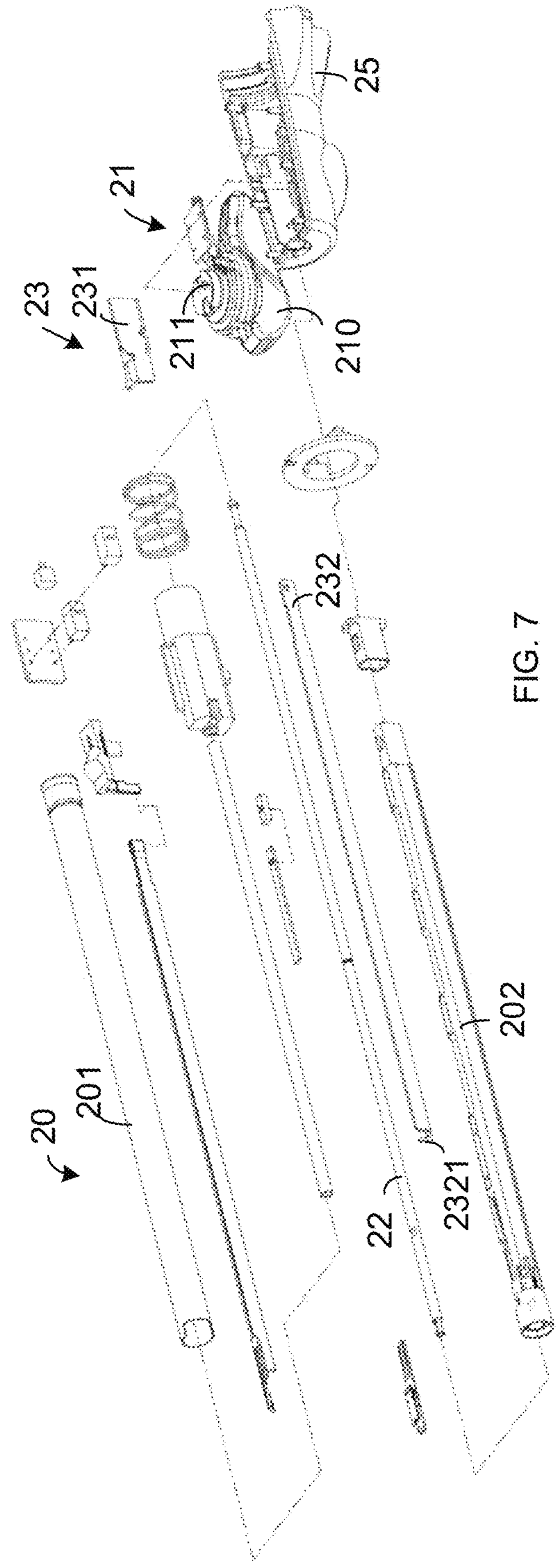
FIG. 7 is an exploded view showing some components of an elongated body assembly of the surgical instrument according to a specific embodiment of the present disclosure.

To achieve articulation of the end effector assembly 30 relative to the longitudinal axis C of the elongate shaft assembly 20 by a set angle, the end-effector assembly 30 includes a proximal body portion 30*a* and a distal execution portion 30*b* that are pivotally connected via an articulation joint 30*c*. Correspondingly, the surgical instrument 100 further includes an articulation drive assembly 21 and an articulation transmission assembly 23 for driving the articulation joint 30*c* to articulate. As shown in FIG. 7, the articulation transmission assembly 23 includes an articulation transmission frame 231 and an articulation link 232. The articulation transmission frame 231 is connected to the proximal end of the articulation link 232, and is operatively connected to the articulation drive assembly 21. The articulation drive assembly 21 includes an articulation knob 210 and an articulation drive member 211 which are mounted on the rotation knob 25. The articulation drive member 211 is connected to the articulation transmission frame 231. Rotation of the articulation knob 210 operated by the operator can drive the articulation drive member 211 to move. Specifically, when the articulation knob 210 is operated to rotate clockwise from an initial position, the articulation drive member 211 drives the articulation link 232 to move toward the distal end, and when the articulation knob 210 is operated to rotate counterclockwise from the initial position, the articulation drive member 211 drives the articulation link 232 to move toward the proximal end; and vice versa.

Figure 5:
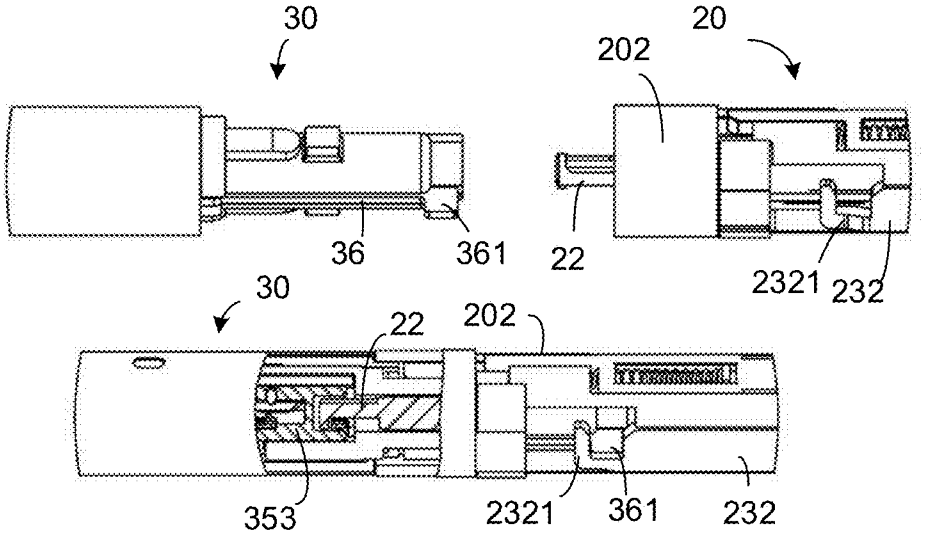
FIG. 5 is a schematic diagram of a connection relationship between an end-effector assembly and the main body portion according to a specific embodiment of the present disclosure.
Figure 6:
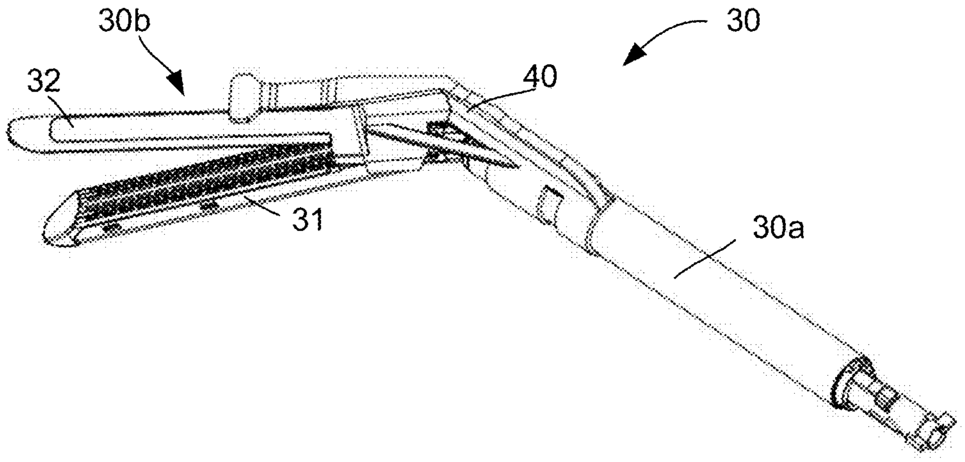
FIG. 6 is a schematic structural diagram of the end-effector assembly according to a specific embodiment of the present disclosure.
Figure 8:
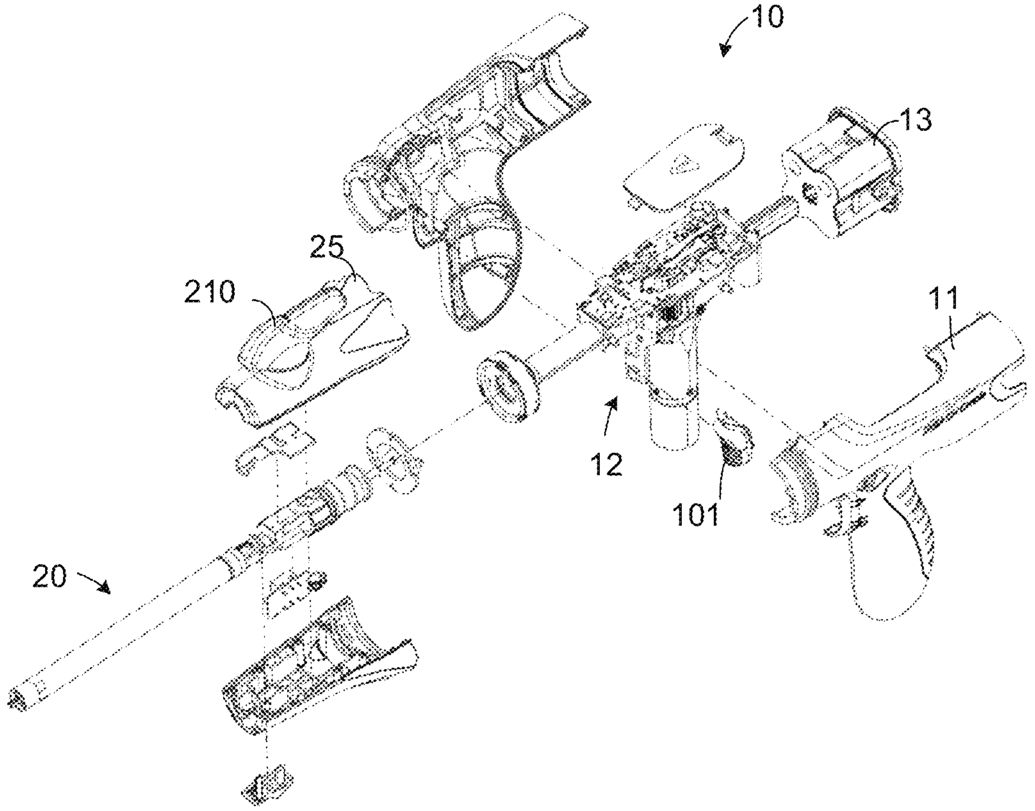
FIG. 8 is an exploded view showing some components of the elongated body assembly and a handle assembly of the surgical instrument according to a specific embodiment of the present disclosure.

The surgical instrument 100 may also manipulate the closing and firing of the distal execution portion 30*b* via a button 101 disposed on the handle assembly 10, so that the distal execution portion 30*b* performs cutting and stapling operations on tissues. Specifically, as shown in FIGS. 7 and 8, the handle assembly 10 includes a drive mechanism 12 disposed in a handle housing 11 to provide output power for the surgical instrument 100. The elongated body assembly 20 includes an outer tube 201, a firing rod 22 is disposed in the outer tube 201, and the firing rod 22 is operably engaged with the drive mechanism 12 so as to be driven by the drive mechanism 12 to perform reciprocating movement along the longitudinal axis C, thereby achieving firing (advancing) and retracting functions of the surgical instrument 100. More specifically, the elongated body assembly 20 includes a support member 202 for slidably supporting the firing rod 22 and the articulation link 232, and the distal end of the support member 202 is provided with a tubular housing for engaging a proximal connecting end of the end-effector assembly 30. Referring to FIG. 5, a connecting piece 361 is disposed at the proximal end of an articulation transmission member 36 of the end-effector assembly 30 and fits with a connecting hook 2321 located at the distal end of the articulation link 232, and a connecting portion 353 is disposed at the proximal end of the firing member 35 in the end-effector assembly 30 and fits with the distal end of the firing rod 22, so as to realize rotational snap-fit engagement and locking between the end-effector assembly 30 and the elongated body assembly 20. In addition, the handle assembly 10 further includes a power supply 13 that provides electrical energy to the drive mechanism 12. The power supply 30 may be replaceable and/or rechargeable.

Figure 9:
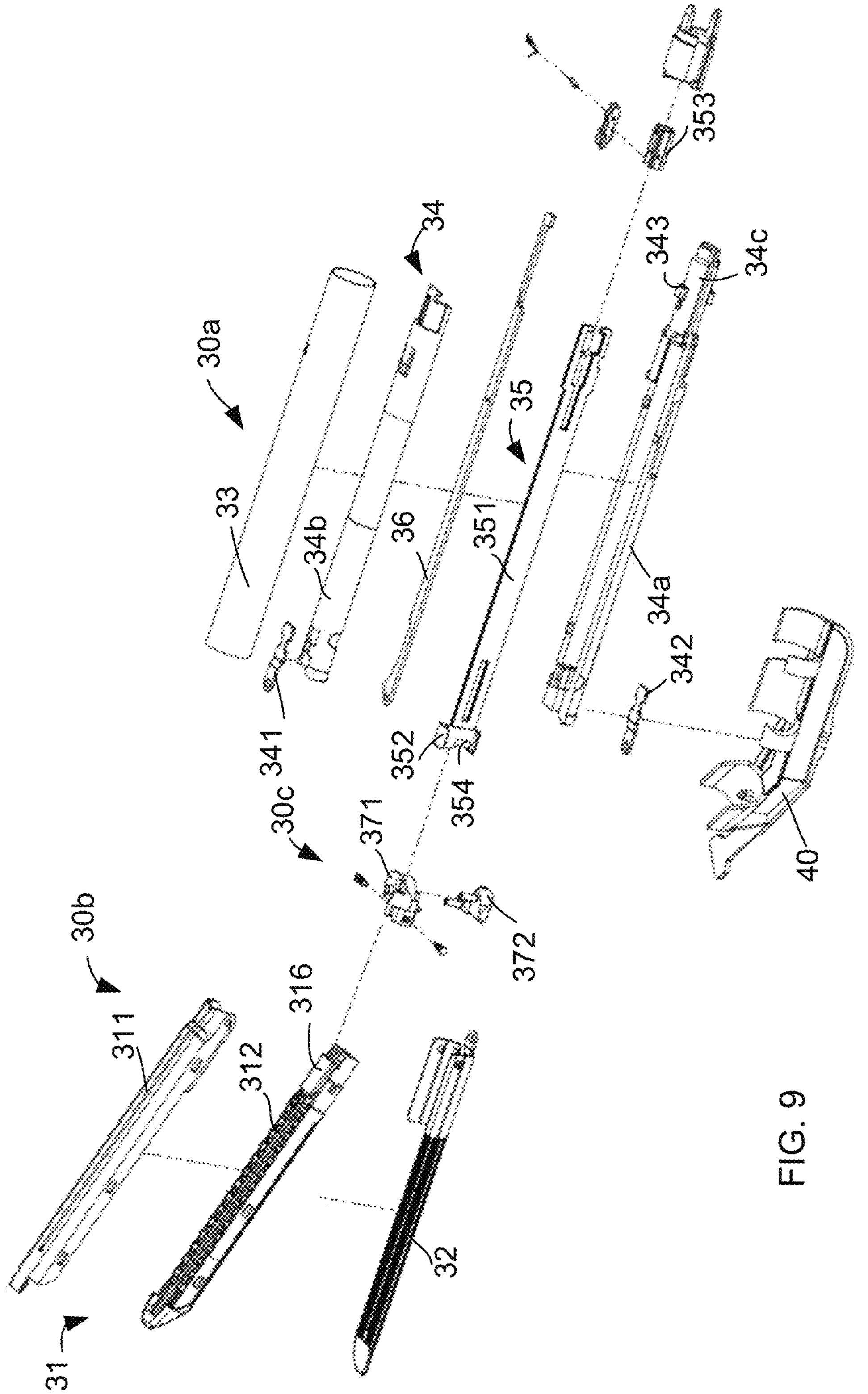
FIG. 9 is an exploded view of the end-effector assembly according to a specific embodiment of the present disclosure.
Figure 10:
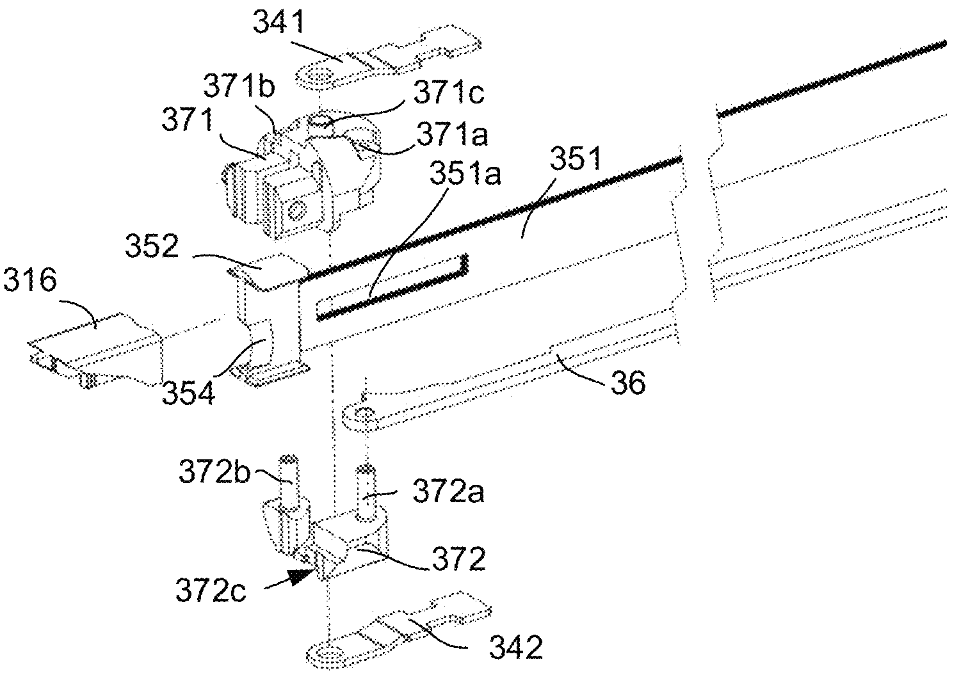
FIG. 10 is an exploded view showing some structures of an articulation joint and a firing member in the end-effector assembly according to a specific embodiment of the present disclosure.

Further referring to FIGS. 9 and 10, a specific embodiment of the end-effector assembly 30 of the surgical instrument 100 of the present disclosure is described in detail. The end-effector assembly 30 is detachably mounted at the distal end of the elongated body assembly 20 of the surgical instrument 100. As previously described, the end-effector assembly 30 includes the proximal body portion 30*a* and the distal execution portion 30*b* that are pivotally connected via the articulation joint 30*c*. The proximal body portion 30*a* of the end-effector assembly 30 may be inserted into the elongated body assembly 20 by being plugged and rotated relative to a housing of the elongated body assembly 20 to lock the end-effector assembly 30 thereon. The staple cartridge assembly 31 and the anvil assembly 32 are movable relative to each other to close the jaws for grasping tissue. In one specific embodiment, the anvil assembly 32 can be operated to pivot toward the staple cartridge assembly 31 until the jaws of the end-effector assembly 30 are closed to clamp tissues; and the anvil assembly 32 pivots in a direction away from the staple cartridge assembly 31 until the jaws of the end-effector assembly 30 are opened to release tissues. In an alternative embodiment, the staple cartridge assembly 31 of the end-effector assembly 30 can be operated to pivot toward the anvil assembly 32 until the jaws of the end-effector assembly 30 are closed to clamp tissues; and the staple cartridge assembly 31 is operated to pivot in a direction away from the staple cartridge assembly 31 until the jaws of the end-effector assembly 30 are opened to release tissues.

The staple cartridge assembly 31 includes a cartridge base 311, a staple cartridge 312, and a drive sled 316 disposed in a cavity between the staple cartridge 312 and the cartridge base 311. Specifically, the cartridge base 311 is connected to the articulation joint 30*c*, and the staple cartridge 312, as a disposable component, is detachably connected within the cartridge base 311. In other alternative embodiments, the cartridge base 311 and the staple cartridge 312 in the staple cartridge assembly 31 may be fixedly connected or may be integrally formed as a component that is detachably connected to the elongated body assembly 20. The cartridge base 311 is formed as an open housing structure having a U-shaped or semi-circular cross-section, which is connected to the distal end of the elongated body assembly 20, and the staple cartridge 312 is inserted into the cartridge base 311 by means of engagement or the like. The staple cartridge 312 is shaped in the form of an elongated seat, one side surface thereof away from the cartridge base 311 is adapted for interacting with tissue, and a cutting blade groove extending from the proximal end to the distal end of the staple cartridge 312 is disposed on the side surface (also referred to as a staple forming surface) of the staple cartridge 312 that is used to interact with the tissue, and the cutting blade groove is suitable for a cutting blade 354 to pass therethrough to cut the tissue clamped between the contact surface and the anvil assembly 32 from the proximal end to the distal end of the staple cartridge 312. In an alternative embodiment, the cutting blade groove is located at an intermediate position on the upper surface of the staple cartridge 312, and the staple cartridge 312 is divided by the cutting blade groove into a first staple forming region and a second staple forming region. The first staple forming region and the second staple forming region of the staple cartridge 312 are respectively provided with at least two rows of staple openings, wherein the number of rows of the staple openings may be two, three, or more according to different surgical conditions. Each row of the staple openings is provided with several columns of openings, the openings are arranged in a longitudinal axis direction of the staple cartridge 312, the openings can be used to receive staples and staple drivers, and the staples are arranged on the respective sides of the staple drivers that face the staple forming surface of the staple cartridge 312. When the drive sled 316 is actuated to slide/move along the longitudinal axis, the staple drivers from the proximal side to the distal side sequentially emplace staples into tissues to achieve staple forming. The anvil assembly 32 includes an anvil cover 321 and an anvil plate disposed within the anvil cover 321. The surface of the anvil plate is provided with a plurality of staple forming pockets. The staple forming pockets correspond one-to-one with the positions of the staple openings on the staple cartridge 312. During tissue stapling, staples ejected from the staple openings contact the staple forming pockets.

Figure 21:
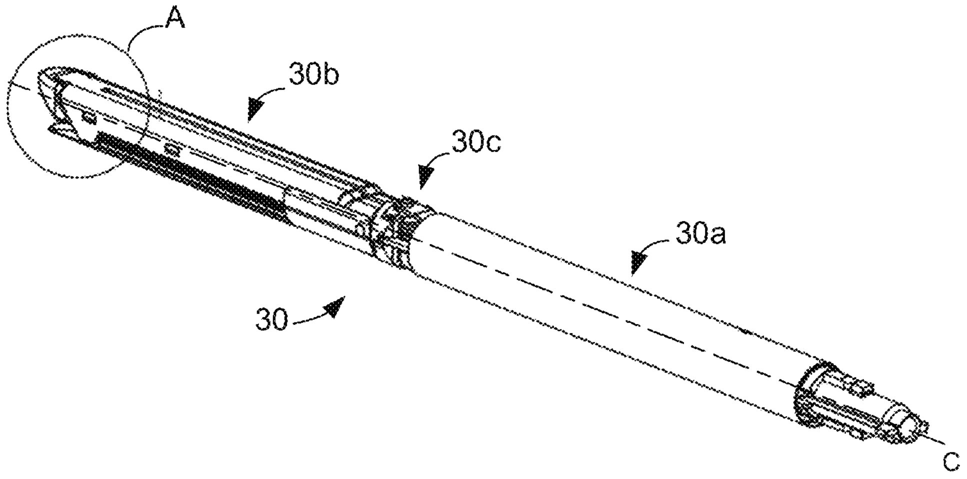
FIG. 21 is an assembly view of the end-effector assembly according to a specific embodiment of the present disclosure.
Figure 22:
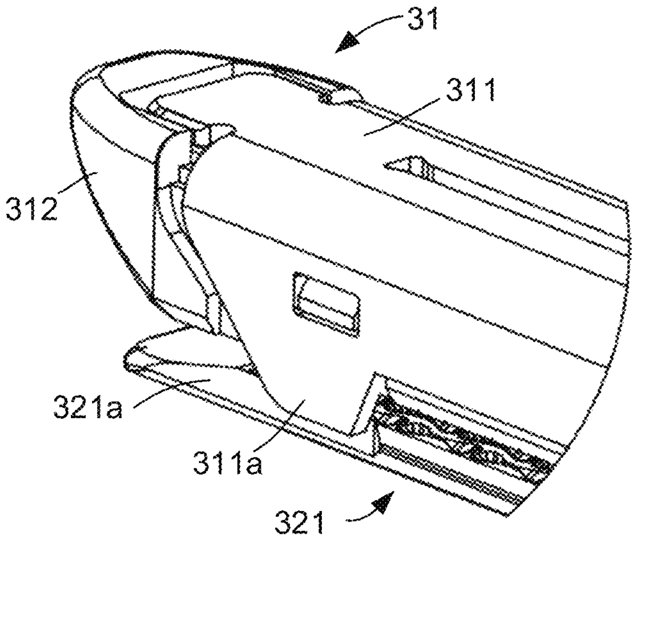
FIG. 22 is an enlarged view of portion A in FIG. 21.
Figure 23:
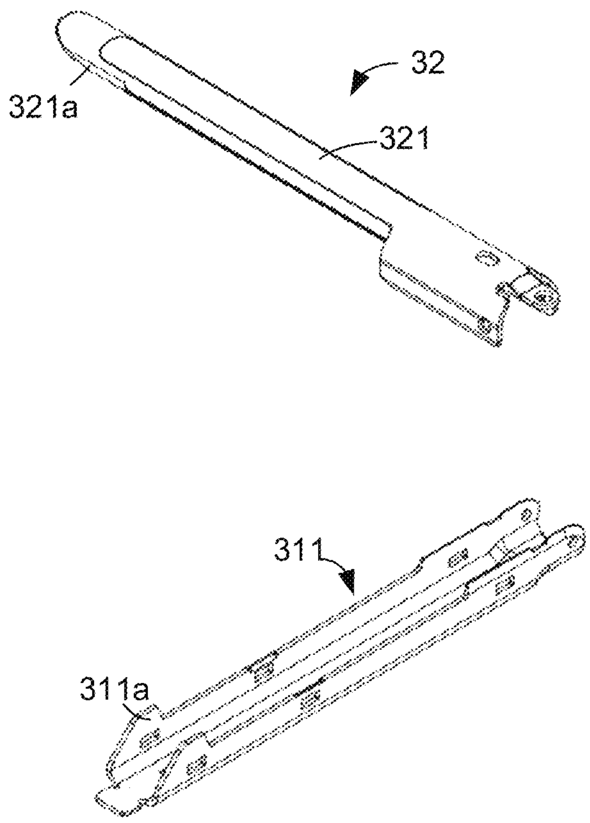
FIG. 23 is a schematic structural diagram of a cartridge base and a staple anvil base in the end-effector assembly according to a specific embodiment of the present disclosure.

In order to prevent the staple cartridge assembly 31 and the anvil assembly 32 located at the distal end from slightly swinging in the width direction when the distal execution portion 30*b* is closed, resulting in a slight misalignment between the staple forming pockets in the anvil assembly and the staple openings in the staple cartridge 312, and ultimately resulting in a poor staple forming effect, the aforementioned end-effector assembly of the present disclosure, positioning structures fitting with each other are disposed at the distal ends of the staple cartridge assembly 31 and the anvil assembly 32, respectively, and the positioning structures are adapted to limit the lateral positions of the staple cartridge assembly 31 and the anvil assembly 32 in the width direction when the distal execution portion is in the closed position. Specifically, in an alternative embodiment, as shown in FIGS. 21-23, the positioning protrusions 311*a* are provided on two side walls of the cartridge base 311 of the staple cartridge assembly 31 in the thickness direction, positioning recesses 321*a* or notch structures are provided at corresponding positions of the anvil cover 321 of the anvil assembly, and the positioning protrusions 311*a* are inserted into the positioning recesses 321*a* to form a positioning structure to limit the position of the staple cartridge assembly 31 in the width direction, so that the two fit with each other at an accurate position and the suturing effect is good. In other alternative embodiments, the positioning protrusion is disposed on the anvil assembly 32 and the positioning recess is disposed on the staple cartridge assembly 31, and the fitting of the two also achieves the function of limiting the positions of the staple cartridge assembly 31 and the anvil assembly 32 in the width direction.

As further shown in FIG. 9, the proximal body portion 30*a* of the end-effector assembly 30 includes an elongated outer tube 33, an inner tube 34 disposed in the outer tube 33, a firing member 35 slidably connected to the inner tube 34, and the articulation transmission member 36. The inner tube 34 is formed by a first half-tube 34*a* and a second half-tube 34*b*, wherein the proximal end of the first half-tube 34*a* includes an engaging portion 34*c* for connecting to the elongated body assembly 20, and an engaging lug 343 is disposed on the engaging portion 34*c* for releasably engaging with the elongated body assembly 20 in a snap-fit connection manner. The first half-tube 34*a* and the second half-tube 34*b* define a sliding channel for slidably receiving the firing member 35. The firing member 35 includes an elongated firing beam 351, and the firing beam 351 may be formed of a single-sheet of deformable material, or preferably formed of a plurality of stacked sheets. A working portion 352 is provided at the distal end of the firing beam 351, and the cutting blade 354 is provided on the working portion 352 for forming an incision on a tissue to be cut during firing, wherein the working portion 352 of the firing member 35 is formed into an I-shaped beam structure, a partial region of which abuts against the slider 316 and the two can slide toward the distal end of the staple cartridge 312 as a whole to perform a corresponding surgical operation. For example, when the firing member 35 is driven to move from the proximal end to the distal end, a partial region of the working portion 352 of the firing member 35 pushes the slider 316 to move toward the distal end together, and the slider 316 acts on the staple drivers to push the staples out of the staple cartridge 312 to achieve the anastomosis operation on the tissue while the cutting blade 354 on the working portion 352 cuts the tissue. The connecting portion 353 is disposed at the proximal end of the firing beam 351. The connecting portion 353 is formed into a sleeve structure with an opening. A hole is provided at the proximal end of the connecting portion 353, and is configured to receive the distal end of the firing rod 22 when the proximal end of the end-effector assembly 30 is engaged with the elongated body assembly 20.

Referring to FIGS. 9 and 10, the articulation joint 30*c* includes a first link 371 and a second link 372, a pivot pin 371*c* is defined on the first link 371, the distal end of the inner tube 34 is fixedly connected to a pivotable support piece 341, and the distal end of the pivotable support piece 341 is pivotably connected to the pivot pin 371*c*, thereby pivotably connecting the articulation joint 30*c* to the proximal body portion 30*a*, and enabling the distal execution portion 30*b* to operably pivot relative to the proximal body portion 30*a*. In an alternative embodiment, in order to improve the stability of the pivotal movement of the distal execution portion 30*b* relative to the proximal body portion 30, corresponding coaxial pivot pins 371*c*, 372*c* are respectively disposed on the first link 371 and the second link 372, and pivotable support pieces 341, 342 are also disposed on the first half-tube 34*a* and the second half-tube 34*b*, respectively. The distal ends of the pivotable support pieces 341, 342 are pivotably connected to their corresponding pivot pins 371*c*, 372, respectively.

With continued reference to FIG. 10, the first link 371 and the second link 372 are connected by means of two connection pins 372*a*, 372*b* located on two opposite sides of the pivot pin 371*c*. Specifically, the connection pins 372*a*, 372*b* are fixedly provided on the second link 372, holes 371*a*, 371*b* corresponding thereto are disposed on the first link 371, and the connection pins 372*a*, 372*b* are fixedly connected to the holes 371*a*, 371*b* on the first link 372 by means of riveting, welding, or the like. Alternatively, in an alternative embodiment, each of the first link 371 and the second link 372 is provided with corresponding holes, and the first link 371 and the second link 372 are fixedly connected by riveting or welding two ends of each of the connection pins 372*a*, 372*b*, respectively. Further, the connecting shaft 372*a* of the articulation joint 30*c* is also adapted for fitting with a hole at the distal end of the articulation transmission member 36, so as to convert movement along the longitudinal axis C provided by the articulation transmission member 36 into a pivotal movement of the articulation joint 30*c* about the pivot pin 371*c* and/or the pivot pin 372*c*. In order to describe the specific technical solution of the present disclosure more clearly, the connecting shaft 372*a* engaged with the articulation transmission member 36 is hereinafter referred to as an articulation drive member 372*a*. The distal end of the articulation transmission member 36 in the proximal body portion 30*a* is pivotably connected to the articulation drive member 372*a*. Next, an articulation process of the end-effector assembly 30 provided in the embodiments of the present disclosure will be described in detail with reference to FIGS. 11-15.

Figure 11A:
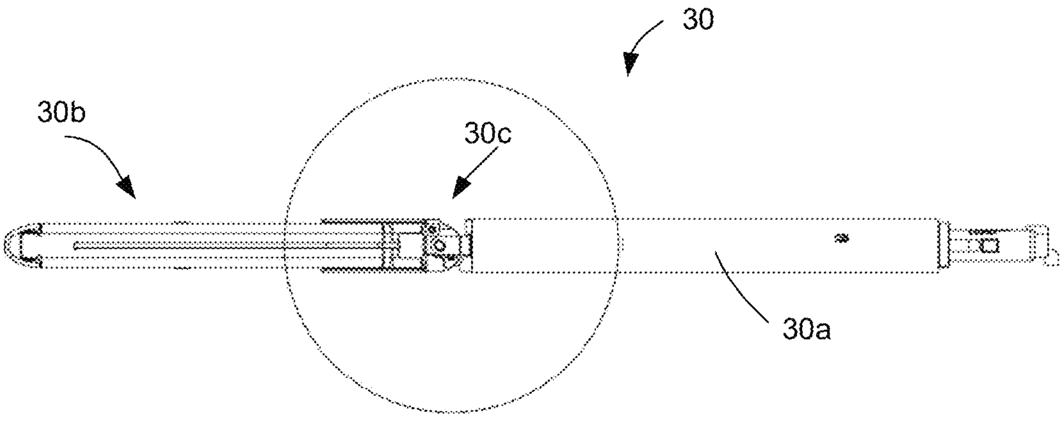
FIGS. 11A-B are schematic structural diagrams of a distal execution portion and a proximal body portion of the end-effector assembly that extend in a same direction according to a specific embodiment of the present disclosure.
Figure 11B:
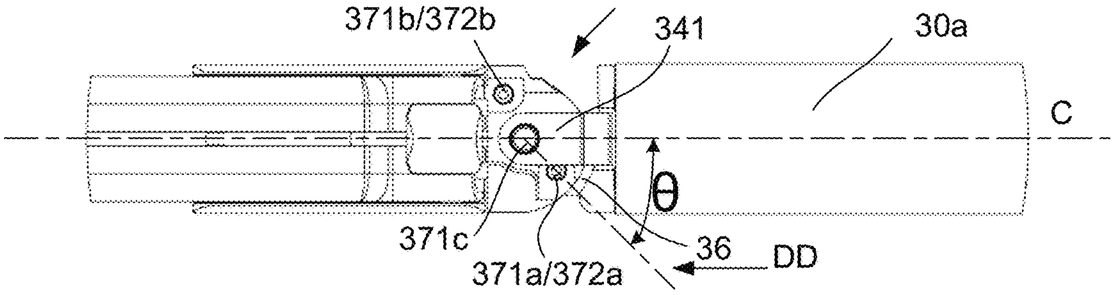
Figure 12A:
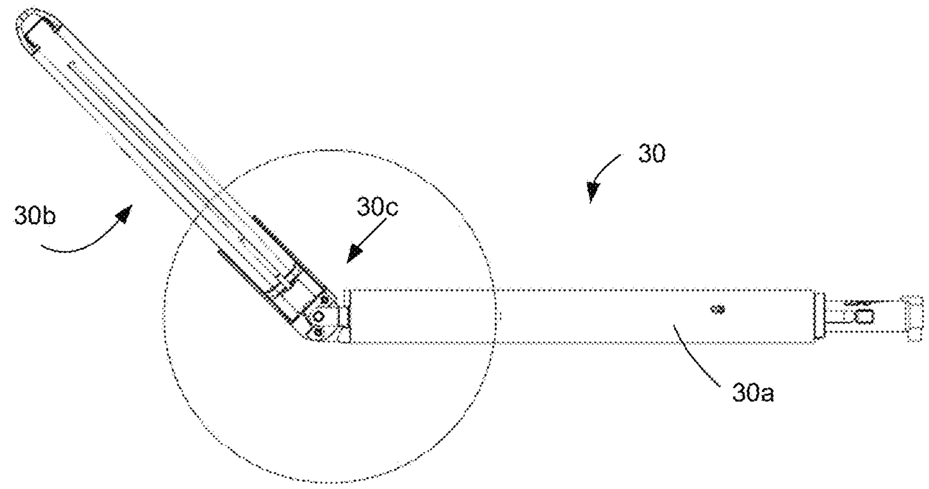
FIGS. 12A-B are schematic structural diagrams of the end-effector assembly in an initial state (ready-to-be-loaded position) according to a specific embodiment of the present disclosure.
Figure 12B:
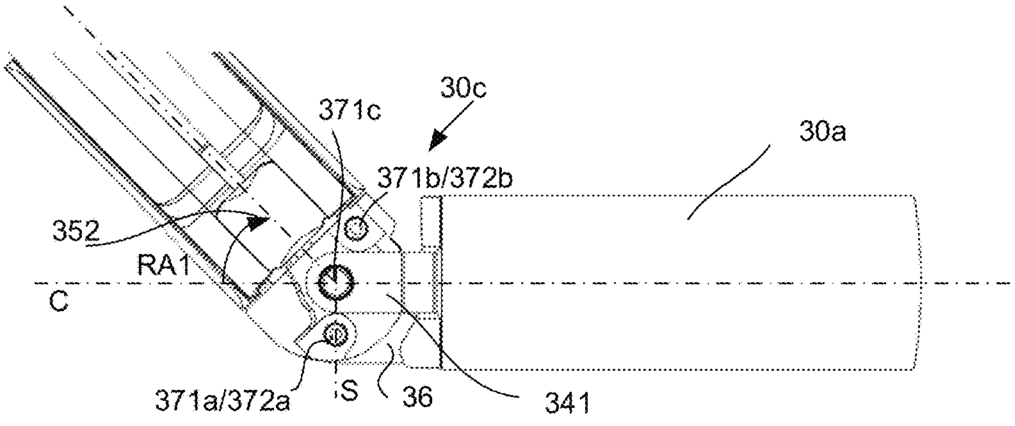
Figure 13A:
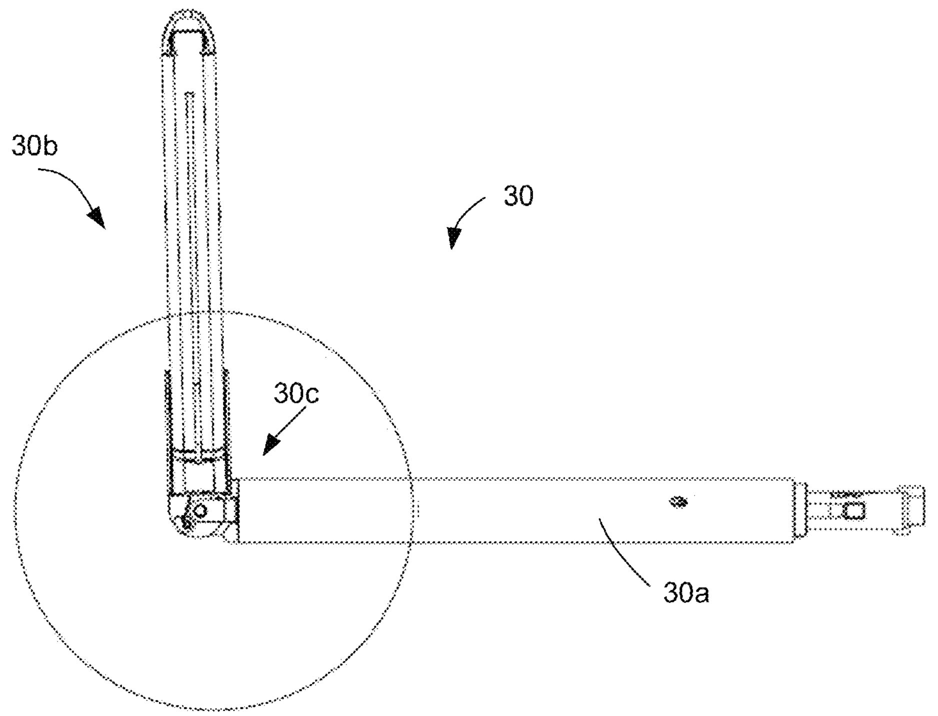
FIGS. 13A-B are schematic structural diagrams of the distal execution portion of the end-effector assembly at a maximum articulation angle according to a specific embodiment of the present disclosure.
Figure 13B:
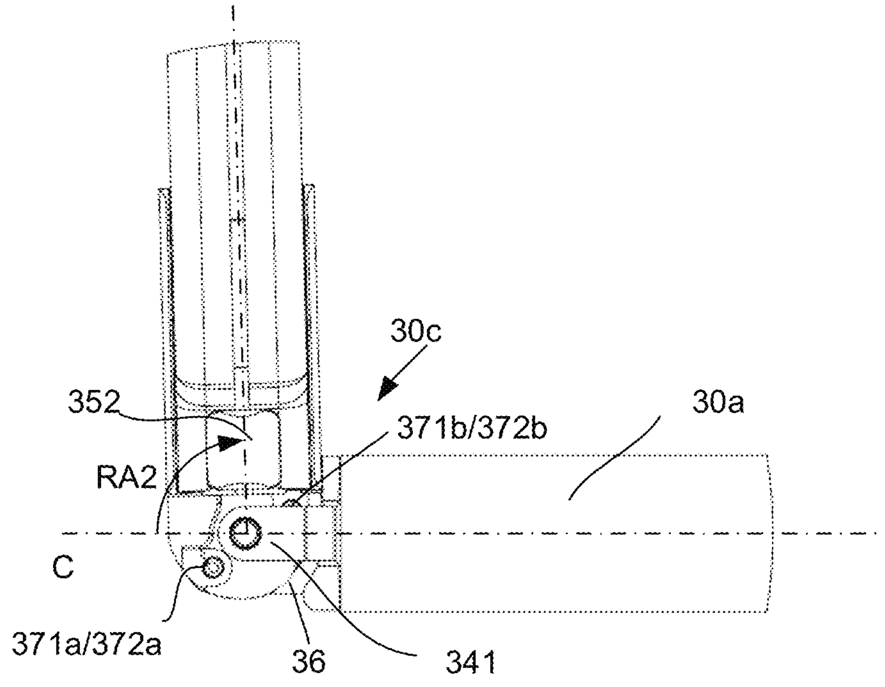

As shown in FIGS. 11A and 11B, when the distal execution portion 30*b* extends along the longitudinal axis C, that is, when the distal execution portion 30*b* extends in the same direction as the proximal body portion 30*a*, an included angle formed by the distal execution portion 30*b* and the longitudinal axis C is 0° or approximately 0°, and the articulation drive member 372*a* is located at the proximal end of the pivot pin 371*c*. The articulation knob 210 of the surgical instrument 100 is operated so that the articulation transmission member 36 is actuated to move distally (in the direction of an arrow DD), driving the articulation drive member 372*a* to pivot about the pivot pin 371*c*, and in such a way, the distal execution portion 30*b* is articulated in a direction gradually away from the longitudinal axis C, and finally reaches a position/state of a maximum articulating angle at one side, as shown in FIGS. 13A and 13B. During the process of the distal execution portion 30*b* articulating in the direction away from the longitudinal axis C, when a certain included angle is reached between the distal execution portion 30*b* and the longitudinal axis C, as shown in FIGS. 12A and 12B, the end-effector assembly 30 according to the embodiments of the present disclosure is in an unloaded or unused initial state/position (hereinafter referred to as a ready-to-be-loaded position). The end-effector assembly 30, when in the ready-to-be-loaded position, may be coupled and plugged into the distal end of the elongated body assembly 20 of the surgical instrument 100.

It can be understood that the maximum articulation angle that can be provided by the end-effector assembly, in addition to being limited by the mechanical interference of related parts in the end-effector assembly, is also limited by a maximum stroke that can be provided by the articulation link 232 in the handle assembly and the elongated body assembly of the surgical instrument.

To enable the end effector assembly 30 of the embodiments of the present disclosure to be compatible with the main body portion (including the handle assembly and the elongated body assembly) of the surgical instrument in the prior art, i.e., to allow the end effector assembly 30 of the present disclosure to be compatible with the same main body portion (handle assembly and elongate shaft assembly) as a prior art end effector assembly 50 (refer to FIG. 1) of the same specification and size, in one specific embodiment, with reference to FIGS. 12A and 12B, when the end-effector assembly 30 is in the ready-to-be-loaded position, and a line S connecting the axis center of the articulation drive member 372*a* and the axis center of the pivot pin 371*c* of the articulation joint 30*c* is perpendicular to the longitudinal axis C, a predetermined first included angle RA1 is formed between the distal execution portion 30*b* and the longitudinal axis C.

Specifically, after the end-effector assembly 30 in the ready-to-be-loaded position is arranged on the elongated body assembly 20 of the surgical instrument 100, the articulation link 232 is caused to move distally by a first distance by operating the articulation knob 210 of the handle assembly 10, and correspondingly, the articulation transmission member 36 is also driven to move distally by L1, so that the distal execution portion 30*b* of the end-effector assembly 30, which has been articulated through the first angle RA1, is further articulated away from the longitudinal axis C to form a second included angle RA2. Similarly, after the end-effector assembly 30 in the ready-to-be-loaded position is arranged on the elongated body assembly 20 of the surgical instrument 100, the articulation link 232 is caused to move proximally by a second distance by operating the articulation knob 210 of the handle assembly 10, and correspondingly, the articulation transmission member 36 is also driven to move proximally by L2, so that the distal execution portion 30*b* of the end-effector assembly 30, which has been articulated through the first included angle RA1, further pivots in a direction close to the longitudinal axis C and ultimately forms an angle of 0° or substantially 0° relative to the longitudinal axis C for better passage of the end-effector assembly 30 through a trocar device, wherein the first distance and the second distance may be the same or different.

When the end-effector assembly 30 according to the embodiments of the present disclosure is adapted to the prior art surgical instrument, the first distance may correspond to a distance moved by the articulation link when the end-effector assembly 50 is articulated rightward to the maximum angle RA, and the second distance may correspond to a distance moved by the articulation link when the end-effector assembly 50 is articulated leftward to the maximum angle LA. The arrangement of the end-effector assembly 30 further broadens the applicability and adaptability of the end-effector assembly according to the embodiments of the present disclosure.

Figure 15A:
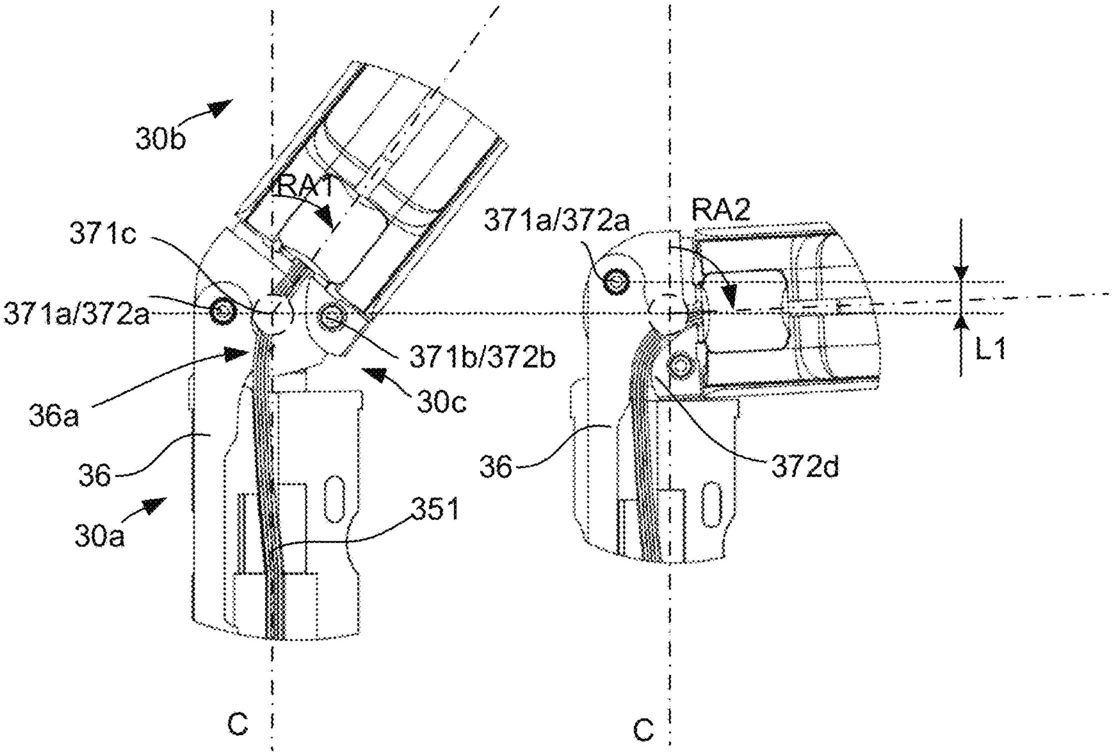
FIG. 15A is a diagram showing a moving distance of an articulation transmission member in the longitudinal axis direction when the end-effector assembly changes from the initial state (ready-to-be-loaded position) to the maximum articulation angle according to a specific embodiment of the present disclosure.
Figure 15B:
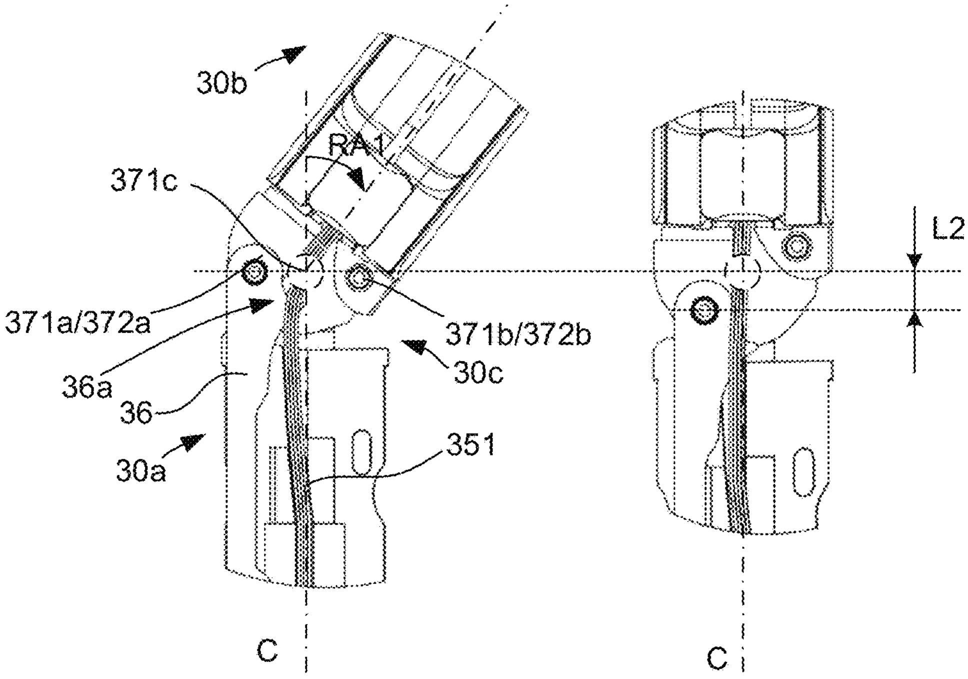
FIG. 15B is a diagram showing a moving distance of the articulation transmission member in the longitudinal axis direction when the end-effector assembly changes from the initial state (ready-to-be-loaded position) to an unarticulated state according to a specific embodiment of the present disclosure.

In one specific embodiment, referring to FIG. 15A, when the articulation knob 210 is operated to rotate clockwise from an initial position to a maximum rotatable position, the articulation link 232 is driven to move distally by the first distance, then the articulation drive member 372*a* is driven to move distally by L1 along the longitudinal axis C, and the distal execution portion 30*b* that has been articulated through the first included angle RA1 is further articulated to the maximum articulation angle RA2. Referring to FIG. 15B, when the articulation knob 210 is operated to rotate counterclockwise from the initial position to the maximum rotatable position, the articulation drive member 211 drives the articulation link 232 to move proximally by the second distance, then the articulation drive member 372*a* is driven to move proximally by L2 along the longitudinal axis C, and the distal execution portion 30*b* that has been articulated through the initial first included angle RA1 is articulated to extend in the same direction as the longitudinal axis C, that is, the articulation angle is 0° or approximately 0°. It can be seen that when the articulation transmission member 36 moves distally by L1+L2 in the longitudinal axis C direction, or in other words, the articulation transmission member 36 is operated to move distally along the longitudinal axis C from a proximal start position to a distal end position, the included angle formed by the distal execution portion 30*b* and the longitudinal axis C ranges from 0° or approximately 0° to the maximum articulation angle RA2.

Figure 16A:
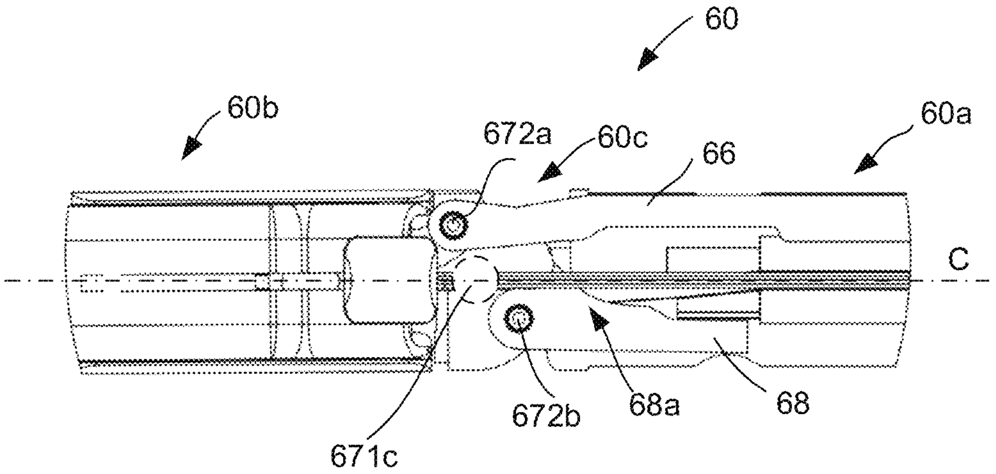
FIG. 16A is a schematic structural diagram of the distal execution portion and the proximal body portion of the end-effector assembly that extend in a same direction according to another specific embodiment of the present disclosure.
Figure 16B:
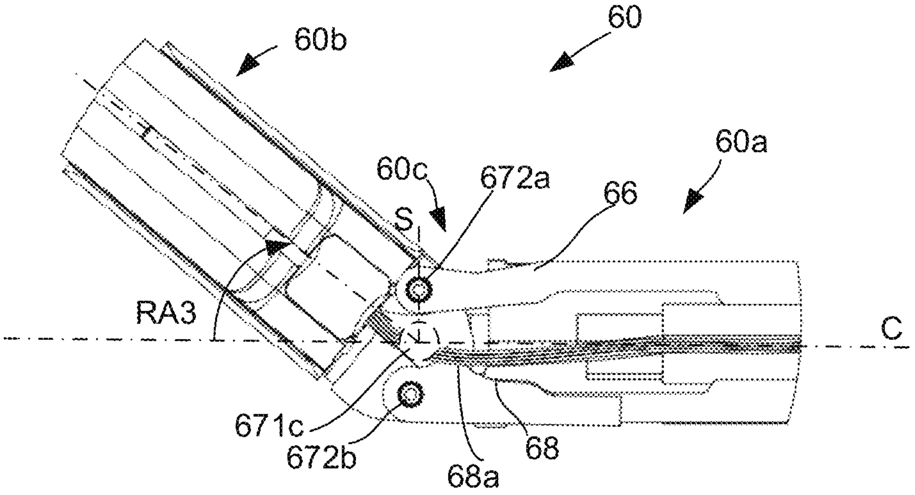
FIG. 16B is a schematic structural diagram of the end-effector assembly in the initial state (ready-to-be-loaded position) according to another specific embodiment of the present disclosure.
Figure 16C:
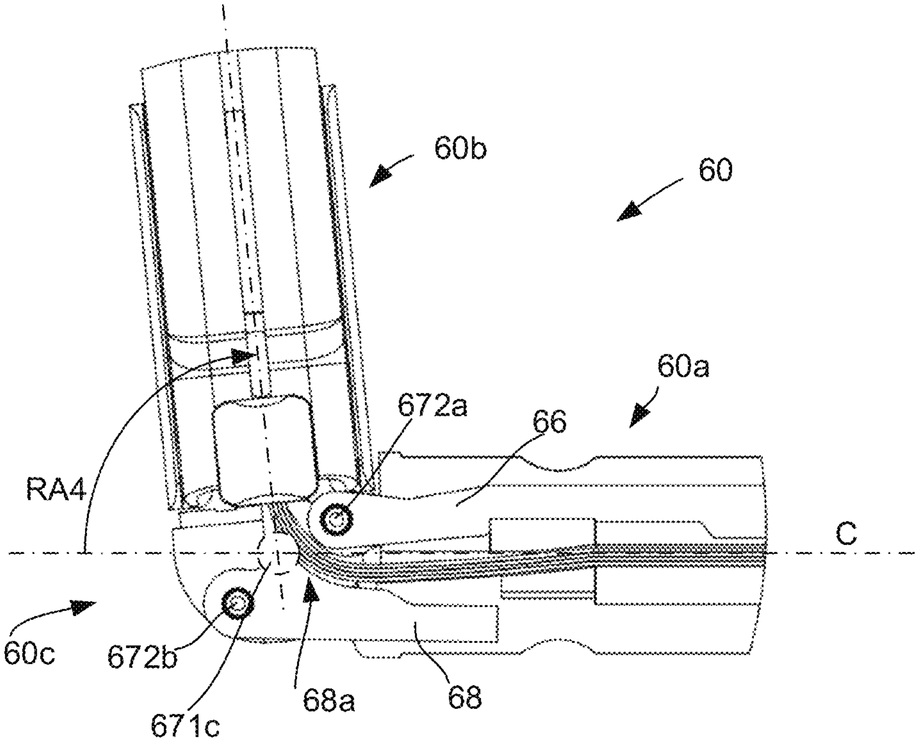
FIG. 16C is a schematic structural diagram of the distal execution portion of the end-effector assembly at the maximum articulation angle according to another specific embodiment of the present disclosure.
Figure 17A:
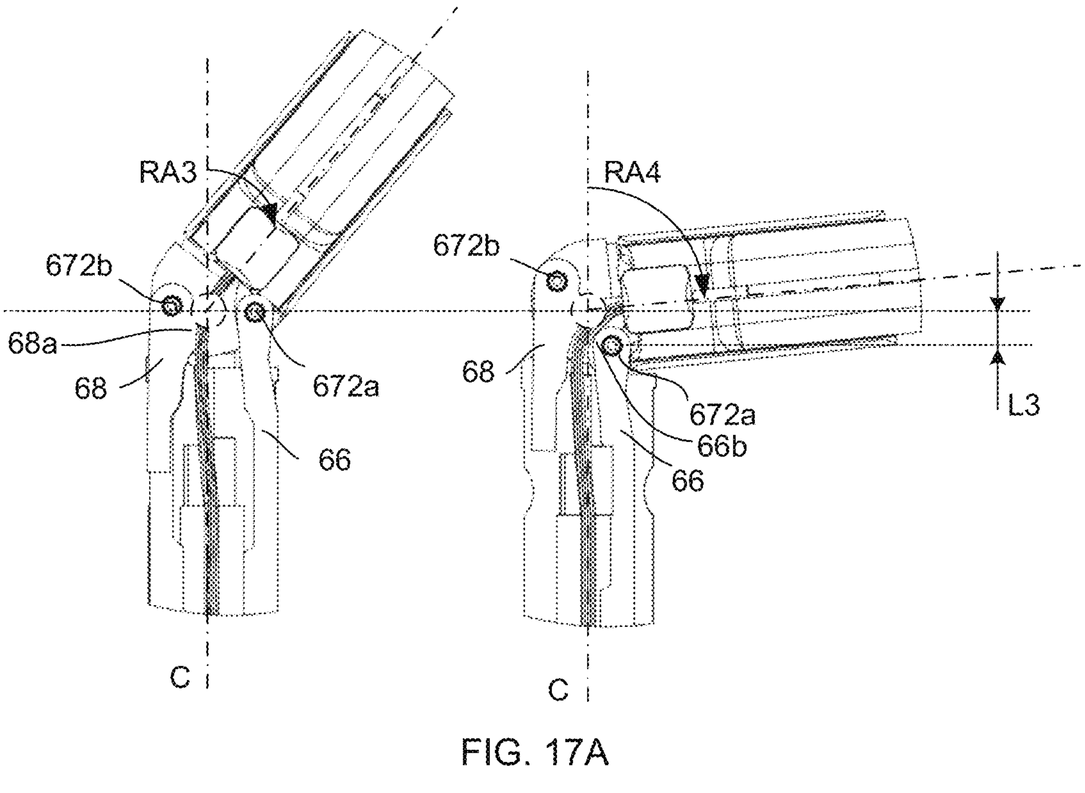
FIG. 17A is a diagram showing a moving distance of the articulation transmission member in the longitudinal axis direction when the end-effector assembly changes from the initial state (ready-to-be-loaded position) to the maximum articulation angle according to another specific embodiment of the present disclosure.
Figure 17B:
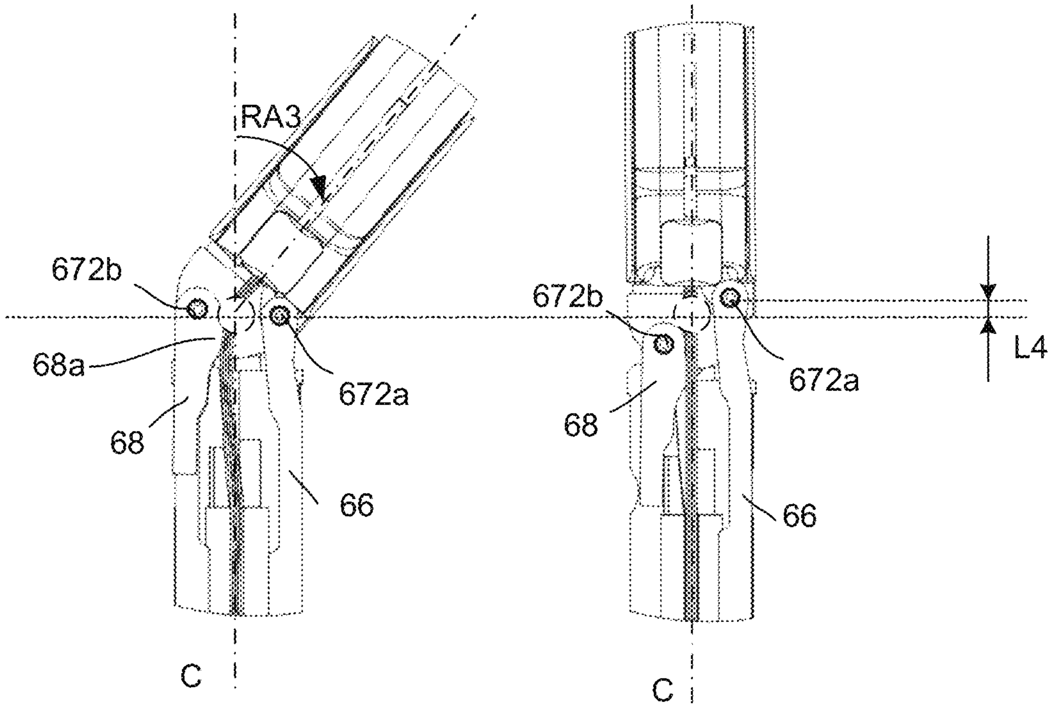
FIG. 17B is a diagram showing a moving distance of the articulation transmission member in the longitudinal axis direction when the end-effector assembly changes from the initial state (ready-to-be-loaded position) to the unarticulated state according to another specific embodiment of the present disclosure.

As shown in FIGS. 16-17, in an alternative embodiment, the articulation drive member 672*a* of the end-effector assembly 60 is pivotably connected to the distal end of the articulation transmission member 66. Articulation of the distal effector portion 60*b* and the articulation joint 60*c* relative to the proximal body portion 60*a* is achieved by the articulation transmission member 66 being operably pulled proximally. Specifically, referring to FIG. 16A, when the angle between the distal effector portion 60*b* and the longitudinal axis C defined by the proximal body portion 60*a* is 0° or approximately 0°, the articulation drive member 672*a* is located distal to the pivot pin 671*c*. The articulation knob 210 is operated to cause the articulation transmission member 66 to move proximally, thereby pulling the articulation drive member 672*a* to pivot about the pivot pin 671*c* and driving the distal execution portion 60*b* to gradually move away from the longitudinal axis C until it is articulated to a maximum angle, referring to FIG. 16C. Similarly, in order to enable the end-effector assembly 60 to be adapted to the main body portion (including the handle assembly and the elongated body assembly) of the prior art surgical instrument and to fully utilize a maximum stroke that the articulation link 232 can provide, the state/position of the end-effector assembly 60 shown in FIG. 16B is defined as an unloaded or unused initial state/position (hereinafter referred to as a ready-to-be-loaded position). At this point, a line S connecting the axis centers of the articulation drive member 672*a* and the pivot pin 671*c* of the end-effector assembly 60 is perpendicular to the longitudinal axis C.

After the end-effector assembly 60 in the ready-to-be-loaded position is arranged on the elongated body assembly 20 of the surgical instrument 100, the articulation link 232 is caused to move proximally by a third distance by operating the articulation knob 210 of the handle assembly 10, and correspondingly, the articulation transmission member 66 is also driven to move proximally by L3 so that the distal execution portion 60*b* of the end-effector assembly 60 which has been articulated through a third included angle RA3 is further articulated away from the longitudinal axis C until a fourth included angle RA4 is formed. Similarly, after the end-effector assembly 60 in the ready-to-be-loaded position is mounted on the elongated body assembly 20 of the surgical instrument 100, the articulation link 232 is caused to move distally by a fourth distance by operating the articulation knob 210 of the handle assembly 10, and correspondingly, the articulation transmission member 66 is also driven to move distally by L4 so that the distal execution portion 60*b* of the end-effector assembly 60 which has been articulated through the third included angle RA3 further pivots in a direction close to the longitudinal axis C, and finally forms 0° or substantially 0° with the longitudinal axis C for better passage of the end-effector assembly 60 through the trocar device, wherein the third distance and the fourth distance may be the same or different.

In a specific embodiment, referring to FIG. 17A, when the articulation knob 210 is operated to rotate clockwise from the initial position to the maximum rotatable position, the articulation link 232 is driven to move proximally by the third distance, then the articulation drive member 372*a* is driven to move proximally by L3 along the direction of the longitudinal axis C, and the distal execution portion 30*b* is articulated to the maximum articulation angle. When the articulation knob 210 is operated to rotate counterclockwise from the initial position to the maximum rotatable position, the articulation drive member 211 drives the articulation link 232 to move distally by the fourth distance, then the articulation drive member 372*a* is driven to move distally by L4 along the direction of the longitudinal axis, and the distal execution portion 30*b* is operated to extend in the same direction as the longitudinal axis C, that is, the articulation angle is 0° or approximately 0°. It can be seen that when the articulation transmission member 36 is actuated to move proximally by L3+L4 along the direction of the longitudinal axis C, or in other words, the articulation transmission member 36 is operated to move proximally along the direction of the longitudinal axis C from the distal start position to the proximal end position, and the included angle formed by the distal execution portion 30*b* and the longitudinal axis C ranges from 0° or approximately 0° to the maximum articulation angle RA4.

Of course, it can be understood that, on the basis of the concept of the present disclosure, the end position of the articulation transmission member 36, 66 is not limited to the position corresponding to the position where the distal execution portion 30*b* extends along the longitudinal axis C, that is, the position where the included angle formed by the distal execution portion 30*b* and the longitudinal axis C is 0° or approximately 0°, but may also form a small included angle with the longitudinal axis C according to actual scenario requirements, whether it is articulated left or right.

Figure 2A:
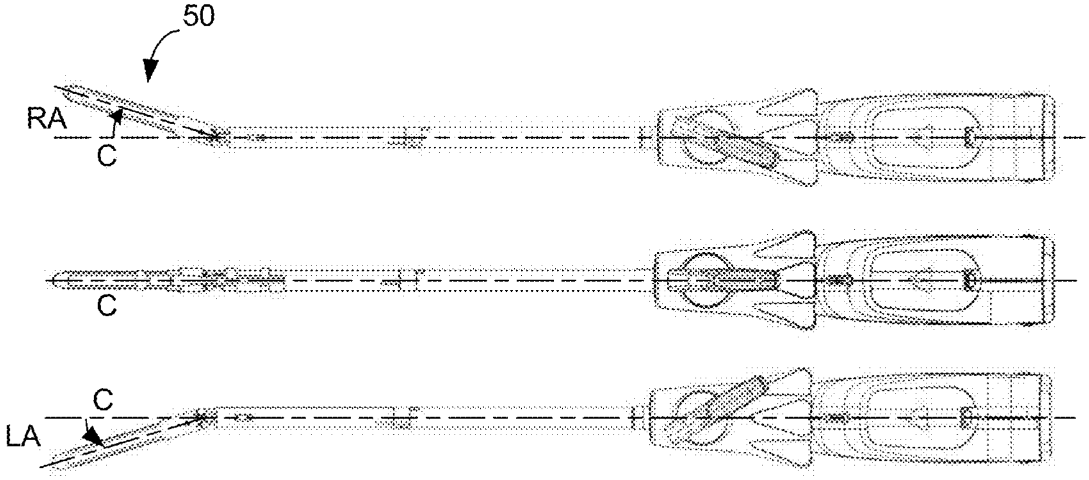
FIG. 2A ( PRIOR ART )
FIG. 2A is a schematic structural diagram of three articulated states of the end-effector assembly of the surgical instrument in the prior art.
Figure 2B:
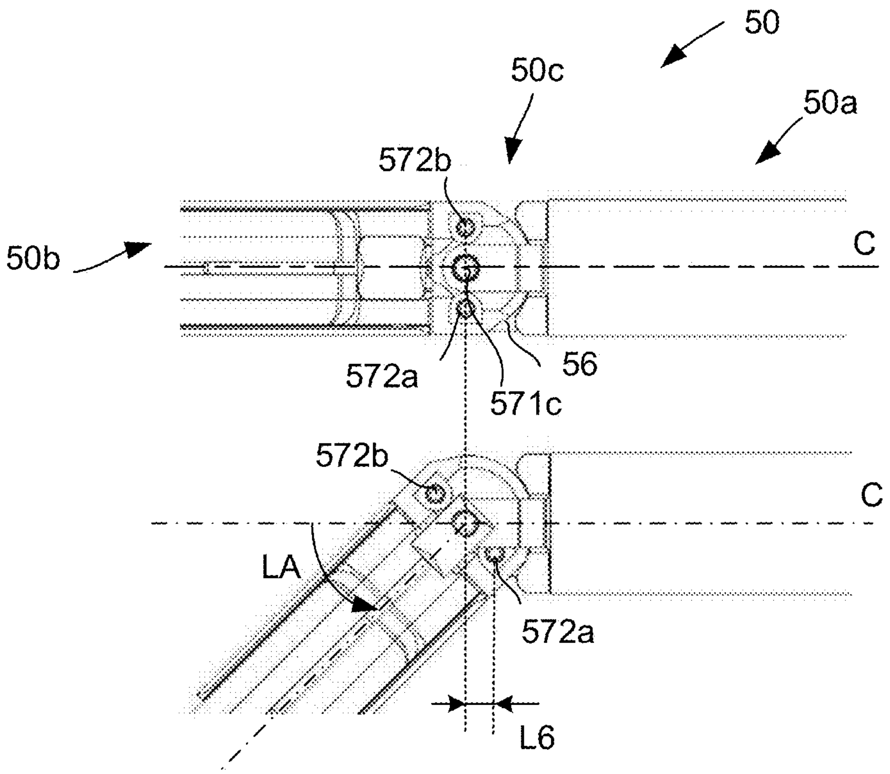
FIG. 2B ( PRIOR ART )
FIGS. 2B-C are diagrams showing a moving distance of an articulation transmission member in a longitudinal axis direction when the end-effector assembly of the surgical instrument in the prior art moves from an initial ready-to-be-loaded position to a maximum articulation angle.
Figure 2C:
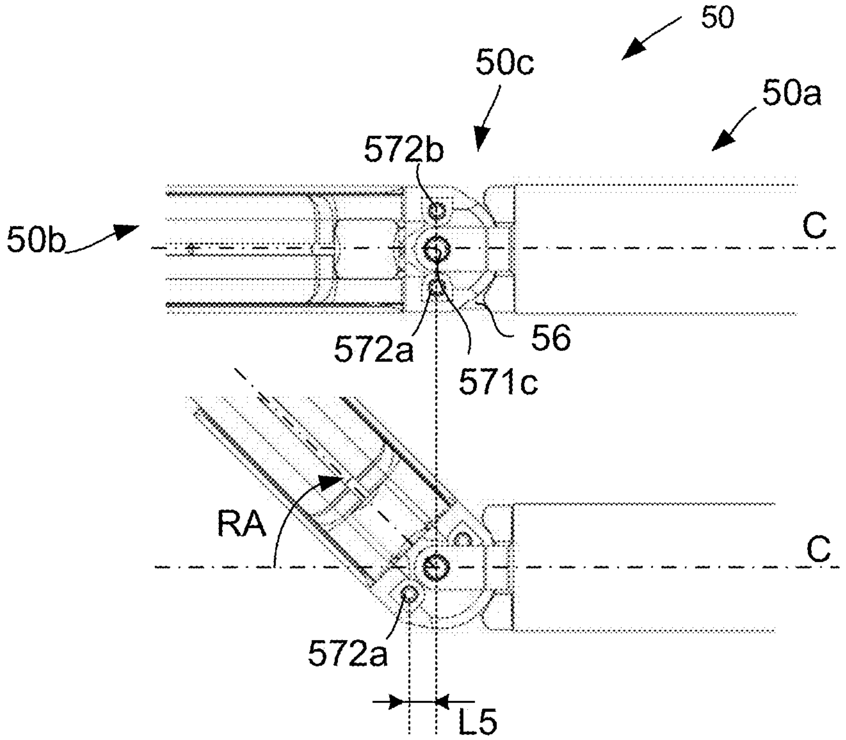
FIG. 2C ( PRIOR ART )

Referring to FIGS. 2B-C, in the end-effector assembly 50 of the prior art, when the articulation knob 210 is operated to rotate clockwise from the initial position to the maximum rotatable position, the articulation link 232 is driven to move distally by a fifth distance, then the articulation transmission member 56 and the articulation drive member 572*a* are driven to move distally by L5 along the direction of the longitudinal axis C, and the distal execution portion 50*b* is articulated clockwise to the maximum articulation angle RA. Referring to FIG. 2C, when the articulation knob 210 is operated to rotate counterclockwise from the initial position to the maximum rotatable position, the articulation link 232 is driven to move proximally by a sixth distance, then the articulation transmission member 56 and the articulation drive member 572*a* are driven to move proximally by L6 in the longitudinal axis C direction, and the distal execution portion 50*b* is articulated counterclockwise to the maximum articulation angle LA. It can be seen that when the articulation transmission member 56 is actuated to move along the direction of the longitudinal axis C by L5 or L6, the included angle formed by the distal execution portion 50*b* and the longitudinal axis C ranges from 0° to the maximum articulation angle RA, LA. As can be seen, when the articulation transmission member 56 is actuated to move proximally by L5+L6 along the direction of the longitudinal axis C from the distal-most position, the included angle formed by the distal execution portion 50*b* and the longitudinal axis C ranges from a maximum articulation angle RA on one side to a maximum articulation angle LA on the other side.

It can be seen that when the maximum movable distances of the articulation transmission members are the same, the structure of the end-effector assembly 30, 60 according to the present disclosure can provide a larger maximum articulation angle than the structure of the prior art end-effector assembly 50.

In any embodiment of the end effector assembly 30, 60 of the present disclosure, when the included angle formed by the distal execution portion 30*b*, 60*b* and the longitudinal axis C is 0°, the line connecting the axis center of the articulation drive member 372*a*, 672*a* and the axis center of the pivot pin 371*c*, 671*c* forms an angle θ with the longitudinal axis C, and the magnitude of θ is one of the factors that determine the maximum articulation angle provided by the end-effector assembly 30, 60. Accordingly, when the end-effector assembly 30, 60 is in the ready-to-be-loaded position, the articulation angle of the distal execution portion 30*b*, 60*b* is (90−θ)°. It can be understood that the smaller the value of θ, the greater the maximum articulation angle that can be provided by the end-effector assembly 30, 60, without considering the mechanical interference of parts and the maximum strokes that can be provided by the articulation drive assembly/articulation transmission assembly. For example, in a specific embodiment, when the included angle formed by the distal execution portion 30*b*, 60*b* and the longitudinal axis C is 0°, the included angle θ formed by a line connecting the shaft centers of the articulation drive member 372*a*, 672*a* and the pivot pin 371*c*, 671*c* and the longitudinal axis C is 45°, which allows the maximum articulation angle of the distal execution portion 30*b*, 60*b* to be about 90°.

When the distal execution portion 30*b*, 60*b* is articulated to a large articulation angle relative to the proximal body portion 30*a*, 60*a*, in order to enable the firing member 35 to be accordingly bent and deformed and smoothly perform a firing operation, the end-effector assembly 30, 60 further includes a constraint channel for limiting movement of the firing beam during firing of the firing member 35 when the distal execution portion 30*b*, 60*b* is in an articulated state, the constraint channel is arranged in a fitting region between the proximal body portion 30*a*, 60*a* and the articulation joint 30*c*, 60*c*, and the firing beam 351 of the firing member 35 is received in the constraint channel and moves in a direction in which the constraint channel extends. The constraint channel is formed by a first constraint portion and a second constraint portion located on opposite sides of the firing beam 351, the first constraint portion is adapted to be engaged with the outer convex arc surface of the firing beam 351 when being most articulated, and the second constraint portion is adapted to be engaged with the inner arc surface of the firing beam 351 when being most articulated.

In any embodiment of the end-effector assembly 30 described in the present disclosure, as shown in FIG. 15A, the first constraint portion is designed as a first constraint protrusion 36*a* disposed on the articulation transmission member 36, and the first constraint protrusion 36*a* has an concave arc surface that matches the outer arc surface of the firing beam 351 when being most articulated (i.e., an outer arc surface of a bending region of the firing beam 351 when the firing beam 351 is articulated to its maximum articulation angle in FIG. 15A). Specifically, the articulation transmission member 36 is formed into an elongated sheet, the first constraint protrusion 36*a* is formed in a partial region of the distal end of the articulation transmission member 36 and protrudes toward the firing member 35, a side surface of the first constraint protrusion 36*a* facing the firing beam 351 forms an concave arc surface, and an arc length of the concave arc surface covers a maximum deformation region of the firing beam 351. The second constraint portion is a second constraint protrusion 372*d* disposed on the articulation joint 30*c*, and the second constraint protrusion 372*d* has an convex arc surface that matches the inner arc surface of the firing beam 351 when being most articulated (i.e., an inner arc surface of a bending region of the firing beam 351 when the firing beam 351 is articulated to its maximum articulation angle). Specifically, the second link 372 of the articulation joint 30*c* is provided with a second constraint protrusion 372*d* near an inner curved region of the firing beam 351, the second constraint protrusion 372*d* has an convex arc surface region, the constraint channel is formed between the articulation transmission member 36 and the second link 372 to limit the articulation position of the firing beam 351, and the firing beam 351 is bent along the constraint channel, preventing it from dislocating sideways during movement of being articulated to high articulation angles. In this embodiment, the articulation transmission member 36 receives articulation driving force directed distally. When driven by the articulation drive mechanism to slide from proximal to distal, the first constraint protrusion 36*a* of the articulation transmission member 36 moves distally into the region of the articulation joint 30*c*, cooperating with the second constraint protrusion 372*d* on the articulation joint 30*c* to form a constraint channel with an approximately 90-degree bend angle.

In any embodiment of the end-effector assembly 60 described in the present disclosure, as shown in FIGS. 16A-C, the first constraint portion includes a constraint member 68 disposed on the proximal body portion 60*a*, and the constraint member 68 has a concave arc surface 68*a* that matches the outer arc surface of the firing beam when being most articulated. Specifically, the proximal end of the constraint member 68 is fixedly connected to an inner tube of the proximal body portion 60*a* and the distal end is sleeved on the connecting shaft 672*b*, and a side thereof close to the firing beam is formed as the concave arc surface 68*a*, wherein an arc length of the concave arc surface 68*a* covers a maximum deformation region of the firing beam. The second constraint portion is a convex arc surface 66*b* disposed at the distal end of the articulation transmission member 66, and the convex arc surface 66*b* matches the inner arc surface of the firing beam when being most articulated.

Figure 14A:
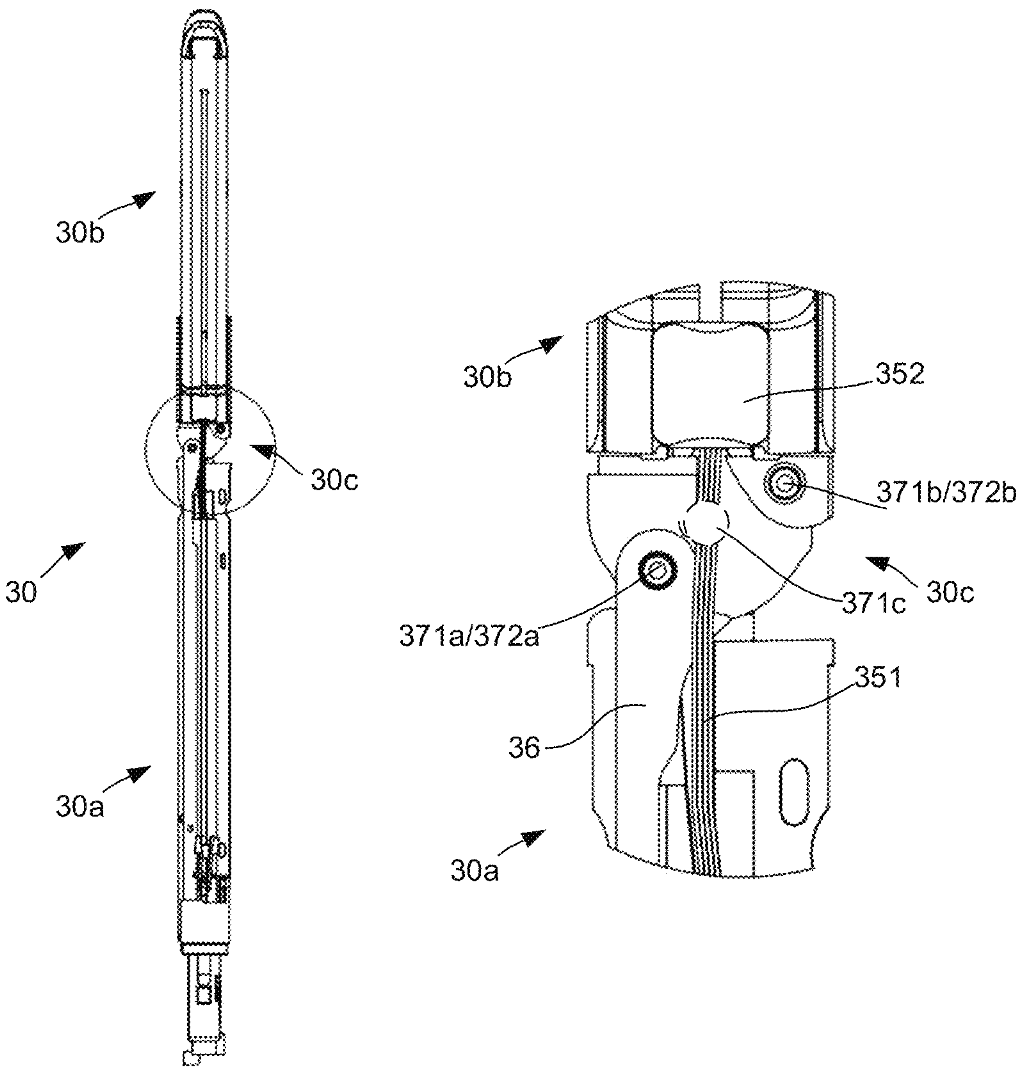
FIG. 14A is another schematic structural diagram of the distal execution portion and the proximal body portion of the end-effector assembly that extend in a same direction according to a specific embodiment of the present disclosure.
Figure 14B:
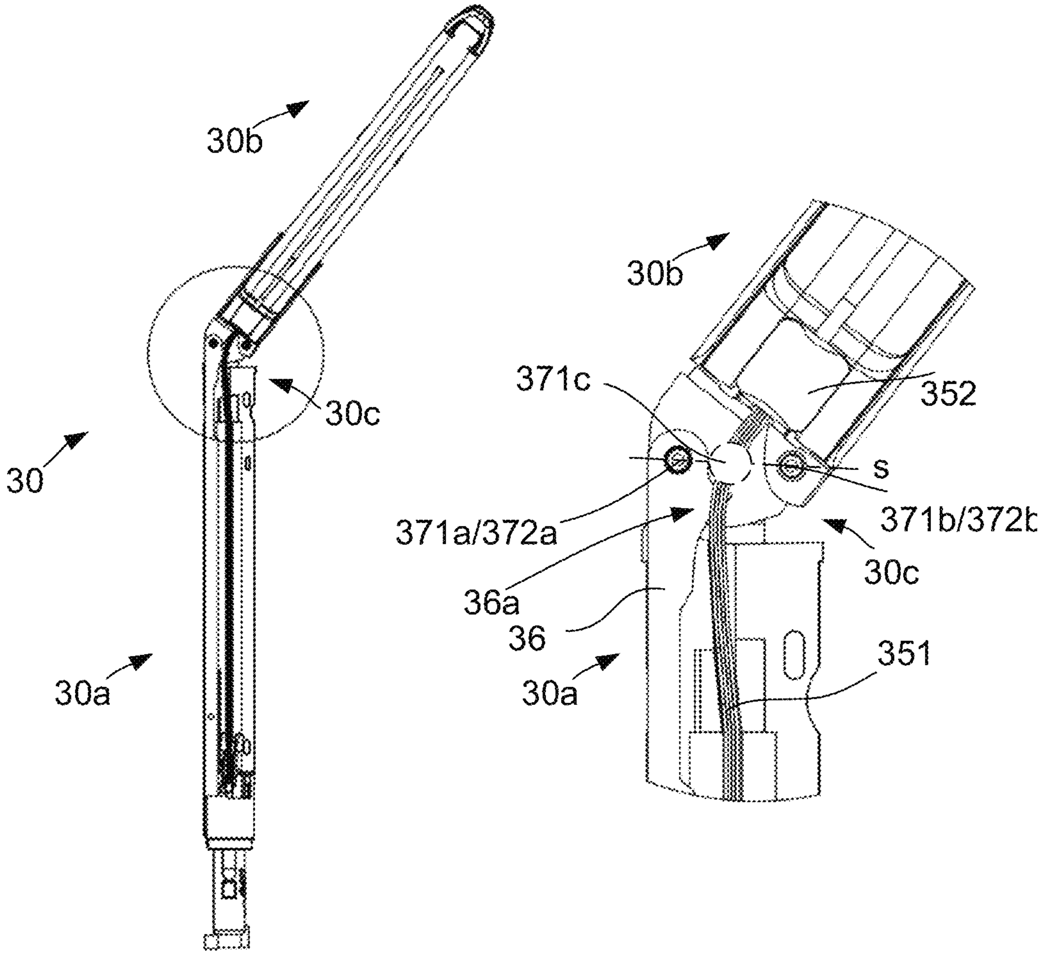
FIG. 14B is another schematic structural diagram of the end-effector assembly in the initial state (ready-to-be-loaded position) according to a specific embodiment of the present disclosure.
Figure 14C:
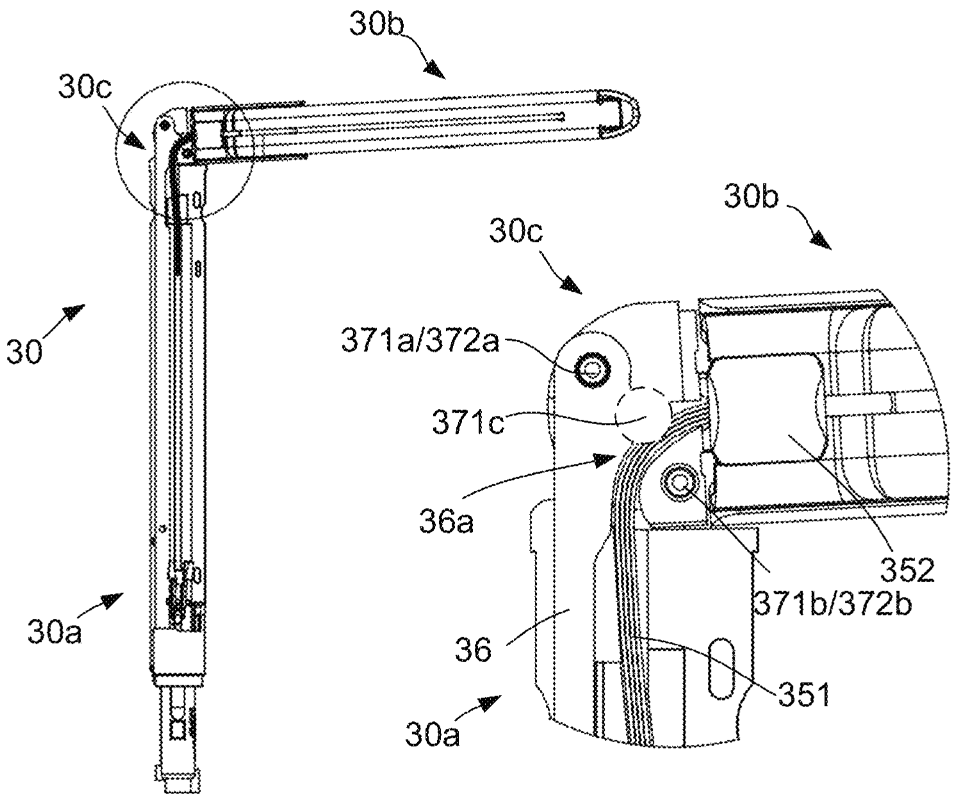
FIG. 14C is another schematic structural diagram of the distal execution portion of the end-effector assembly at the maximum articulation angle according to a specific embodiment of the present disclosure.

As shown in FIG. 10, a receiving slot 351*a* is provided in the distal portion of the firing beam 351 of the firing member 35, and when the articulation angle of the distal execution portion 30*b* is less than a set value, as shown in FIGS. 14A and 16A, a partial region of the first constraint portion is received in the receiving slot 351*a*.

In any of the above-described embodiments of the present disclosure, when the distal execution portion 30 is operated to extend along the direction of the longitudinal axis C, the articulation drive member 371*a*, 372*a* is located proximal or distal to the pivot pin 371*c*, 372*c*. The distal execution portion 30*b* is operated to articulate unidirectionally away from the longitudinal axis C, articulatable between a unarticulated (or straight) position (i.e., a position where the included angle formed by the distal execution portion 30*b*, 60*b* and the longitudinal axis C is 0° or approximately 0°), an intermediate articulated position, and a most articulated position, enabling large-angle unidirectional articulation of the end effector assembly of the surgical stapling instrument.

Furthermore, the end effector assembly 30, 60 provided by any embodiment of the present disclosure still employs a single pivot pin articulation method, ensuring the smallest possible bend radius, or in other words, increasing the maximum articulation angle achievable by the end effector assembly without increasing its bend radius.

Figure 18:
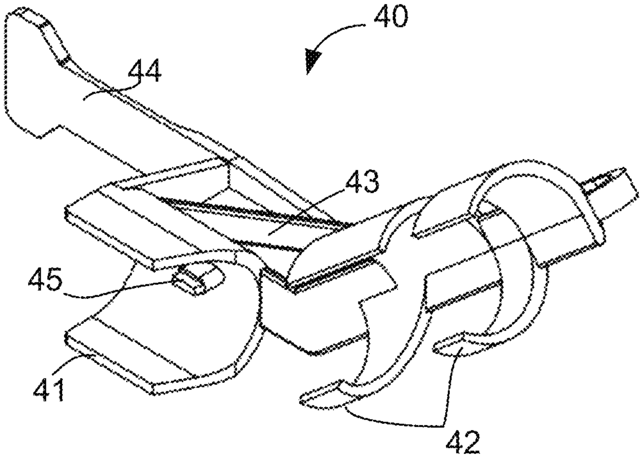
FIG. 18 is a schematic structural diagram of an initial position retainer according to a specific embodiment of the present disclosure.
Figure 19:
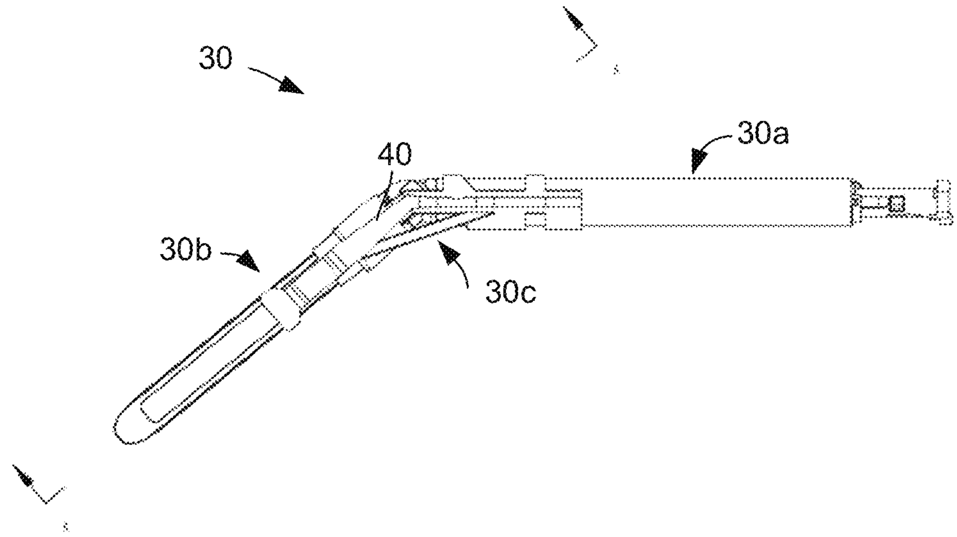
FIG. 19 is a top view of the initial position retainer according to a specific embodiment of the present disclosure.
Figure 20:
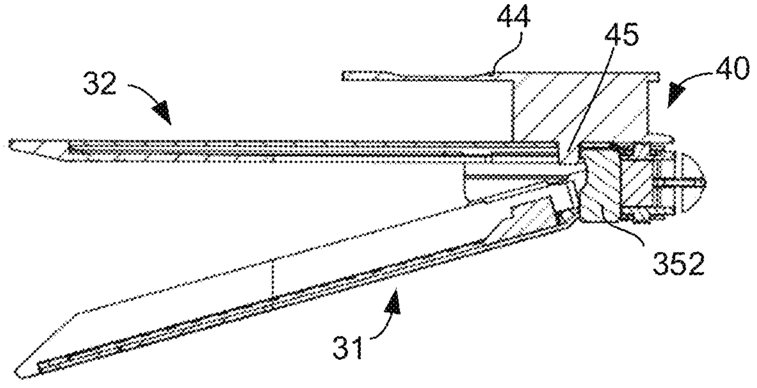
FIG. 20 is a sectional view taken along line A-A in FIG. 19.

Since the ready-to-be-loaded position of the end-effector assembly 30, 60 provided in any embodiment of the present disclosure is a position where the distal execution portion 30*b*, 60*b* forms a certain included angle θ with the longitudinal axis C, the present disclosure further provides an initial retainer so that the end-effector assembly 30, 60 is more reliably retained in the ready-to-be-loaded position. As shown in FIGS. 18 to 20, this is a specific embodiment of the initial position retainer 40 according to the present disclosure. The initial position retainer 40 has a support body having a set angle so that the distal execution portion 30*b*, 60*b* of the end-effector assembly 30, 60 is retained in an initial articulated state for loading. Specifically, the initial position retainer 40 is used to support the distal execution portion 30*b* and the proximal body portion 30*a* of the end-effector assembly 30 so that the distal execution portion 30*b* is retained in an initial articulated state at a set angle relative to the proximal body portion 30*a*. Specifically, the support body includes a first holding arm 41 being engaged with the proximal body portion 30*a* and a second holding arm 42 being engaged with the distal execution portion 30*b*, and further includes a supporting beam 493 connected between the first holding arm 41 and the second holding arm 42, wherein the first holding arm 41 and the second holding arm 42 are formed in a half-ring shape that is semi-open and matches the shapes of the proximal body portion 30*a* and the distal execution portion 30*b*, which are held on the two to prevent separation.

More specifically, in order to facilitate gripping by a user, the initial position retainer 40 further includes a grip frame 44 suitable for the operator to grip, the grip frame 44 is connected to the outer side wall of the support body, and the structure of the grip frame 44 is not unique. In an alternative manner, the grip frame is formed into a hand-grip member suitable for the hand to pass through, and the hand-grip member runs through the entire longitudinal side wall of the support body and extends to an outer side region of the support body to form a cantilever structure. More specifically, the inner wall of the second holding arm 42 of the initial position retainer 40 is provided with a position-limiting structure for fitting with the working portion 352 of the firing member 35. As shown in FIGS. 18-20, the position-limiting structure is a protrusion structure 45 formed on the inner wall of the second holding arm 42, and the protrusion structure 45 extends into the staple anvil base along a through-hole of the staple anvil base 321 and abuts against the working portion 352 of the firing member 35 to prevent the firing member 35 from moving toward the distal end.

Figure 24:
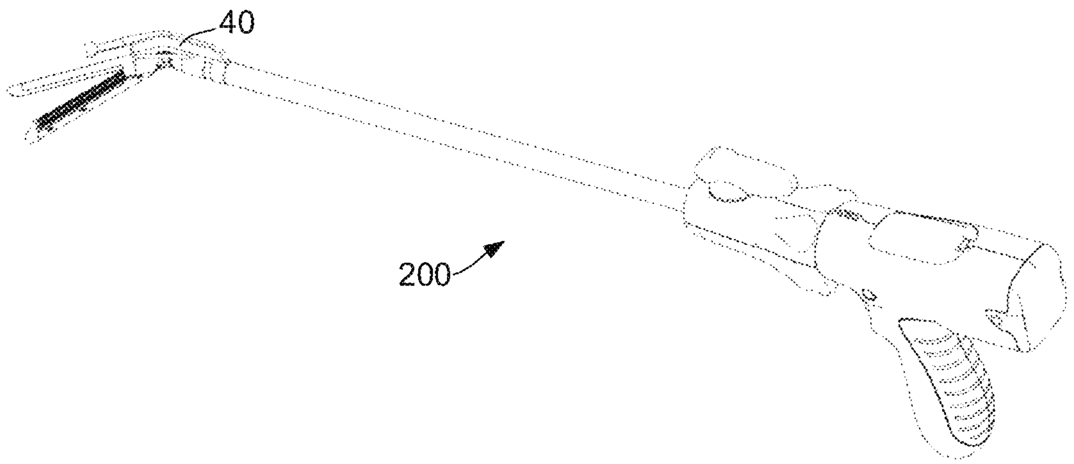
FIG. 24 is a schematic structural diagram of a surgical instrument according to another specific embodiment of the present disclosure.
Figure 25:
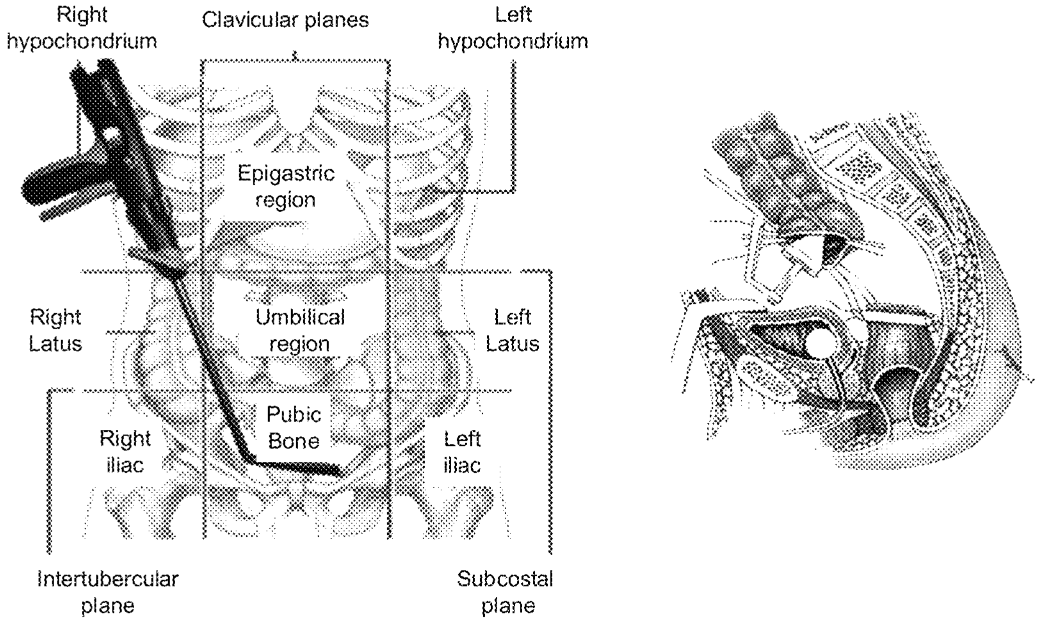
FIG. 25 is a schematic diagram of an LAR surgical procedure.

It can be understood that the end-effector assembly and the initial position retainer provided according to any embodiment of the present disclosure, in addition to being applicable to universal surgical stapling instruments, that is, the entire end-effector assembly is detachably mounted to an elongated body assembly of a surgical instrument, for example, the surgical instrument 100 provided according to any embodiment of the present disclosure, may be applicable to fixed-fit surgical stapling instruments, that is, a proximal body portion of the end-effector assembly is non-detachably fixed to an elongated body assembly of a surgical instrument, while portions of a staple cartridge assembly are detachably replaceable, for example, the surgical instrument 200 shown in FIG. 24.

Obviously, the above-described embodiments are merely examples for clarity of description and are not intended to limit the embodiments. For those of ordinary skill in the art, other different forms of variations and modifications can be made based on the above description. It is not necessary and impossible to list all embodiments here. Obvious variations and modifications derived therefrom are within the scope of protection of the present disclosure.

What is claimed is:

1. An end-effector assembly, comprising:

a proximal body portion that defines a longitudinal axis; and a distal execution portion adapted to manipulate tissue, wherein the distal execution portion being pivotally connected to the proximal body portion through an articulation joint provided with a pivot pin thereon; characterized in that the proximal body portion comprises an articulation transmission member, and an articulation drive member is arranged on the articulation joint, wherein the articulation transmission member is pivotably connected to the articulation drive member, and the articulation transmission member is operable to perform reciprocating movement along the direction of the longitudinal axis to actuate the articulation drive member to pivot about the pivot pin and to actuate the distal execution portion to pivot about the pivot pin, wherein the distal execution portion is operated to articulate unidirectionally to one side away from the longitudinal axis, and is articulable between an unarticulated position, an intermediate articulated position, and a most articulated position; and when the end-effector assembly is in a ready-to-be-loaded position, the distal execution portion being located at the intermediate articulated position, the distal execution portion forms an included angle not equal to 0° relative to the longitudinal axis.

2. The end-effector assembly according to claim 1, wherein when the distal execution portion is operated to extend along the direction of the longitudinal axis, a line connecting an axis center of the articulation drive member and an axis center of the pivot pin forms an angle not equal to 0° with respect to the longitudinal axis.

3. The end-effector assembly according to claim 1, wherein when the distal execution portion is operated to extend along the direction of the longitudinal axis, the articulation drive member is located proximal or distal to the pivot pin.

4. The end-effector assembly according to claim 1, wherein when the end-effector assembly is in the ready-to-be-loaded position, the articulation joint is pivoted so that a line connecting an axis center of the articulation drive member and an axis center of the pivot pin is perpendicular to the longitudinal axis.

5. The end-effector assembly according to claim 1, wherein when the articulation transmission member is operated to move from a start position to an end position, the distal execution portion is actuated to pivot about the pivot pin and to be gradually articulated away from the longitudinal axis.

6. The end-effector assembly according to claim 5, wherein when the articulation transmission member is in the start position, the distal execution portion is operated to extend along the direction of the longitudinal axis.

7. The end-effector assembly according to claim 5, wherein when the end-effector assembly is in the ready-to-be-loaded position, the articulation transmission member is located in an intermediate position that is between the start position and the end position.

8. The end-effector assembly according to claim 1, further comprising a constraint channel adapted to limit an articulation position of a firing member during a firing motion when the distal execution portion is in an articulated state, the constraint channel being arranged in a fitting region between the proximal body portion and the articulation joint, and the firing member being arranged in the constraint channel and movable in a direction in which the constraint channel extends.

9. The end-effector assembly according to claim 8, wherein the constraint channel is formed by a first constraint portion and a second constraint portion arranged on opposite sides of the firing member, respectively.

10. The end-effector assembly according to claim 9, wherein the first constraint portion comprises a first constraint protrusion disposed on the articulation transmission member, the first constraint protrusion has a concave arc surface matching an outer convex arc surface of the firing member when being most articulated, the second constraint portion comprises a second constraint protrusion disposed on the articulation joint, and the second constraint protrusion has a convex arc surface matching an inner concave arc surface of the firing member when being most articulated.

11. The end-effector assembly according to claim 9, wherein the first constraint portion comprises a constraint member disposed on the proximal body portion, the constraint member has a concave arc surface matching an outer convex arc surface of the firing member when being most articulated, the second constraint portion is a convex arc surface provided at the distal end of the articulation transmission member, and the convex arc surface matches an inner convex arc surface of the firing member when being most articulated.

12. The end-effector assembly according to claim 10, wherein a receiving slot is provided in a distal portion of the firing member, and when an articulation angle of the distal execution portion is less than a set value, a partial region of the first constraint portion is received in the receiving slot.

13. The end-effector assembly according to claim 1, wherein the articulation joint comprises a first link and a second link, the pivot pin being disposed on the first link and/or the second link, the first link and the second link are connected through two connection pins located on opposite sides of the pivot pin, and one of the connection pins is adapted for the articulation drive member for cooperating with the articulation transmission member.

14. The end-effector assembly according to claim 1, further comprising an initial position retainer adapted to support the distal execution portion and the proximal body portion so that the distal execution portion is retained in an initial articulated state forming a set angle with respect to the proximal body portion.

15. The end-effector assembly according to claim 14, wherein the initial position retainer comprises a support body having a set angle, and the support body comprises a first holding arm being engaged with the proximal body portion and a second holding arm being engaged with the distal execution portion, and further comprises a supporting beam being connected between the first holding arm and the second holding arm.

16. The end-effector assembly according to claim 14, wherein the initial position retainer is provided with a position-limiting structure for being engaged with the firing member, wherein the position-limiting structure is adapted for being engaged with a working portion of the firing member to limit the position of the firing member.

17. The end-effector assembly according to claim 1, wherein the distal execution portion comprises a staple cartridge assembly and an anvil assembly that are pivotally connected, distal portions of the staple cartridge assembly and the anvil assembly are respectively provided with cooperating positioning structures, the positioning structures being configured to limit lateral positions of the staple cartridge assembly and the anvil assembly along a width direction when the distal effector portion is in a closed position.

18. The end-effector assembly according to claim 17, wherein the positioning structures comprise a positioning protrusion disposed on one of the staple cartridge assembly and the anvil assembly, and a positioning recess disposed on the other of the staple cartridge assembly and the anvil assembly.

* * * * *